United States Patent
Kirschning et al.

(10) Patent No.: US 9,556,439 B2
(45) Date of Patent: Jan. 31, 2017

(54) AGONISTS AND ANTAGONISTS OF TOLL-LIKE RECEPTOR (TLR) 13

(71) Applicant: Bavarian Nordic A/S, Kvistgaard (DK)

(72) Inventors: Carsten Kirschning, Essen (DE); Stefan Bauer, Marbury-Michelbach (DE); Hubertus Hochrein, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

(21) Appl. No.: 14/377,035

(22) PCT Filed: Feb. 8, 2013

(86) PCT No.: PCT/EP2013/000392
§ 371 (c)(1),
(2) Date: Aug. 6, 2014

(87) PCT Pub. No.: WO2013/117348
PCT Pub. Date: Aug. 15, 2013

(65) Prior Publication Data
US 2014/0377309 A1    Dec. 25, 2014

Related U.S. Application Data

(60) Provisional application No. 61/597,063, filed on Feb. 9, 2012.

(51) Int. Cl.
| | | |
|---|---|---|
| *C12N 15/117* | (2010.01) | |
| *A61K 39/39* | (2006.01) | |
| *C12N 15/113* | (2010.01) | |
| *A61K 31/7105* | (2006.01) | |
| *A61K 39/085* | (2006.01) | |
| *A61K 39/09* | (2006.01) | |

(52) U.S. Cl.
CPC ....... *C12N 15/1138* (2013.01); *A61K 31/7105* (2013.01); *A61K 39/085* (2013.01); *A61K 39/092* (2013.01); *A61K 39/39* (2013.01); *C12N 15/117* (2013.01); *C12N 2310/14* (2013.01); *C12N 2310/17* (2013.01); *C12N 2320/30* (2013.01); *C12N 2330/10* (2013.01)

(58) Field of Classification Search
None
See application file for complete search history.

(56) References Cited

U.S. PATENT DOCUMENTS

| | | | | |
|---|---|---|---|---|
| 6,943,240 B2* | 9/2005 | Bauer | ............... | C07K 14/705 435/320.1 |
| 8,153,141 B2* | 4/2012 | Lipford | ............... | A61K 31/205 424/184.1 |
| 8,623,353 B1* | 1/2014 | Kirschning | ............... | 424/130.1 |
| 8,658,607 B2* | 2/2014 | Lipford | ............... | A61K 31/205 435/375 |
| 9,089,508 B2* | 7/2015 | Jackson | ............... | A61K 39/00 |
| 9,090,897 B2* | 7/2015 | Hochrein | ............... | A61K 35/15 |
| 2012/0258082 A1* | 10/2012 | Hochrein | ............... | A61K 35/15 424/93.7 |
| 2014/0135487 A1* | 5/2014 | Lipford | ............... | A61K 31/205 536/23.1 |
| 2014/0343256 A1* | 11/2014 | Kirschning | ......... | C07K 16/2896 530/387.3 |
| 2014/0377309 A1* | 12/2014 | Kirschning | ........... | C12N 15/117 424/243.1 |

FOREIGN PATENT DOCUMENTS

| | | |
|---|---|---|
| WO | WO 98/52962 A1 | 11/1998 |
| WO | WO 01/42457 A2 | 6/2001 |
| WO | WO 01/70955 A2 | 9/2001 |
| WO | WO 2007/048046 A2 | 4/2007 |
| WO | WO 2007/117686 A2 | 10/2007 |

OTHER PUBLICATIONS

Fieber et al, PLoS One, Mar. 10, 2015, 10/3:e0119727 20 pages.*
Hidmark et al, J. Immunol., 2012, 189:2717-2721, prepublished online Aug. 15, 2012.*
Hochrein et al, OncoImmunology, 2013, 2:3, e23141; published online: Mar. 1, 2013.*
Kruger et al, EMBO Reports (2015) 16: 1656-1663; published online Nov. 6, 2015.*
Li et al, eLife 2012;1:e00102. DOI: 10.7554/eLife.00102; 14 pages; published: Oct. 30, 2012.*
Signorino et al, Infection and Immunity, Dec. 2014 vol. 82 No. 12, p. 5013-5022.*
Shi et al, A Novel Toll-like Receptor That Recognizes Vesicular Stomatitis Virus, Journal of Biological Chemistry published online Dec. 3, 2010, 286 (6), 4517-4524.
Oldenburg et al., "TLR13 Recognizes Bacterial 23S rRNA Devoid of Erythromycin Resistance—Forming Modification" Science, Aug. 31, 2012 337 (6098), 1111-1115.
International Search report for PCT/EP2013/000392 dated Jun. 20, 2013.
Written Opinion of the International Search Authority for PCT/EP2013/000392, dated Jun. 20, 2013.

* cited by examiner

*Primary Examiner* — Nita M Minnifield

(57) ABSTRACT

The present invention relates to the field of immunology. The present invention provides agonists and antagonists of Toll-like receptor (TLR) 13. In particular, the present invention provides TLR13 activating and inhibiting nucleic acids, and provides such nucleic acids for use as pharmaceutical agents. The present invention further provides in vitro methods using such nucleic acids.

6 Claims, 8 Drawing Sheets

Figure 1:
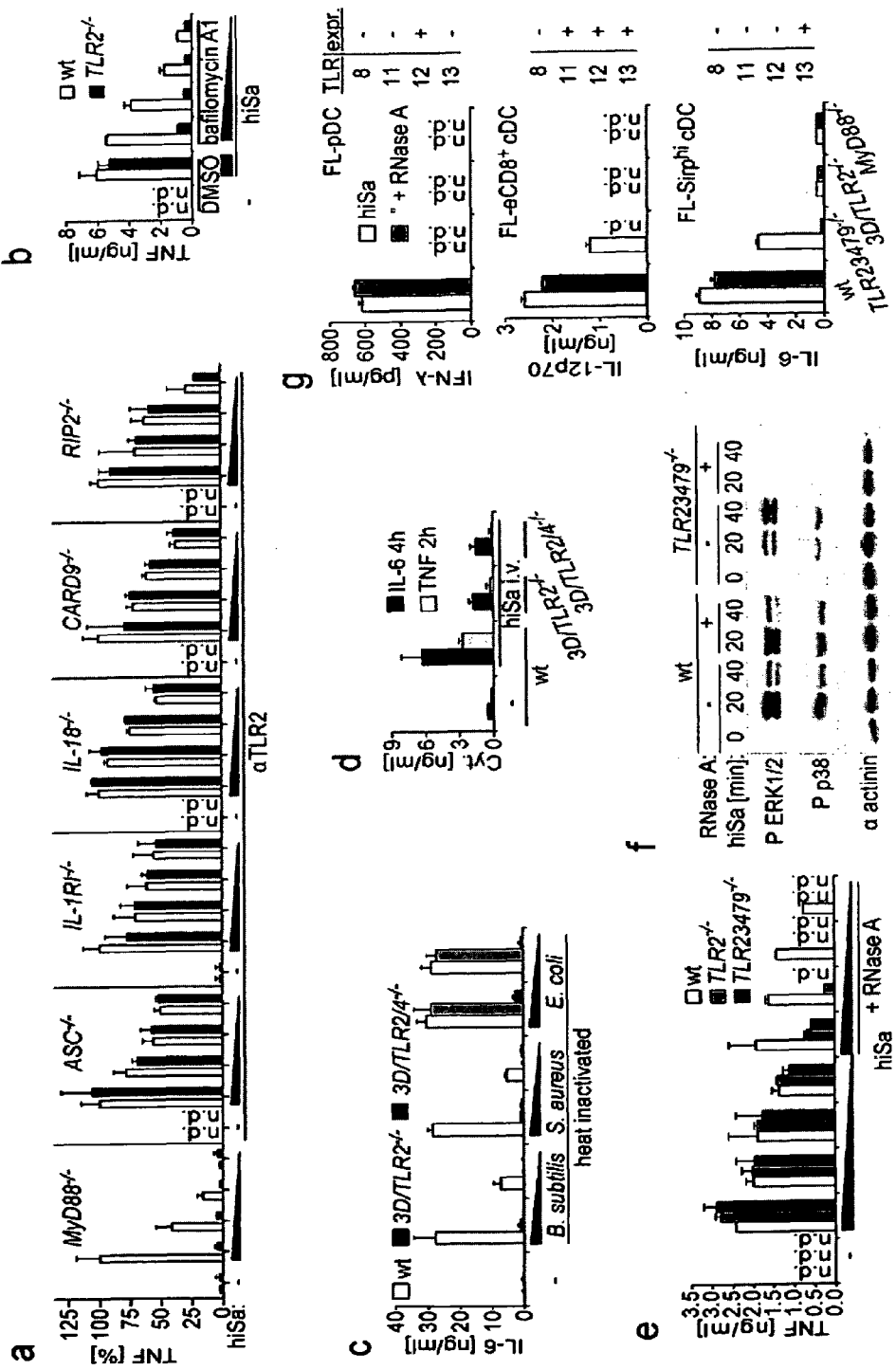

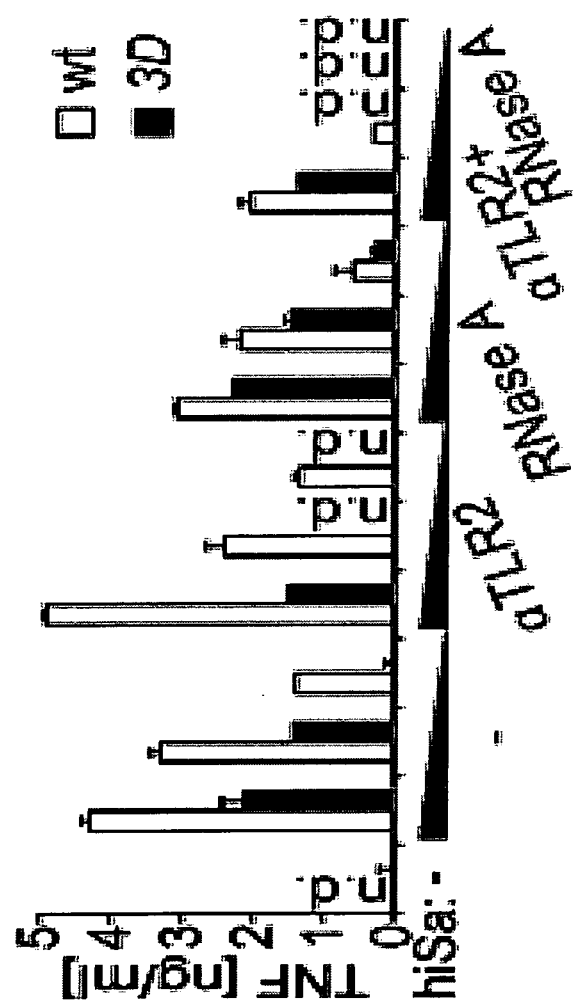
Figure 1.1

Figure 2:
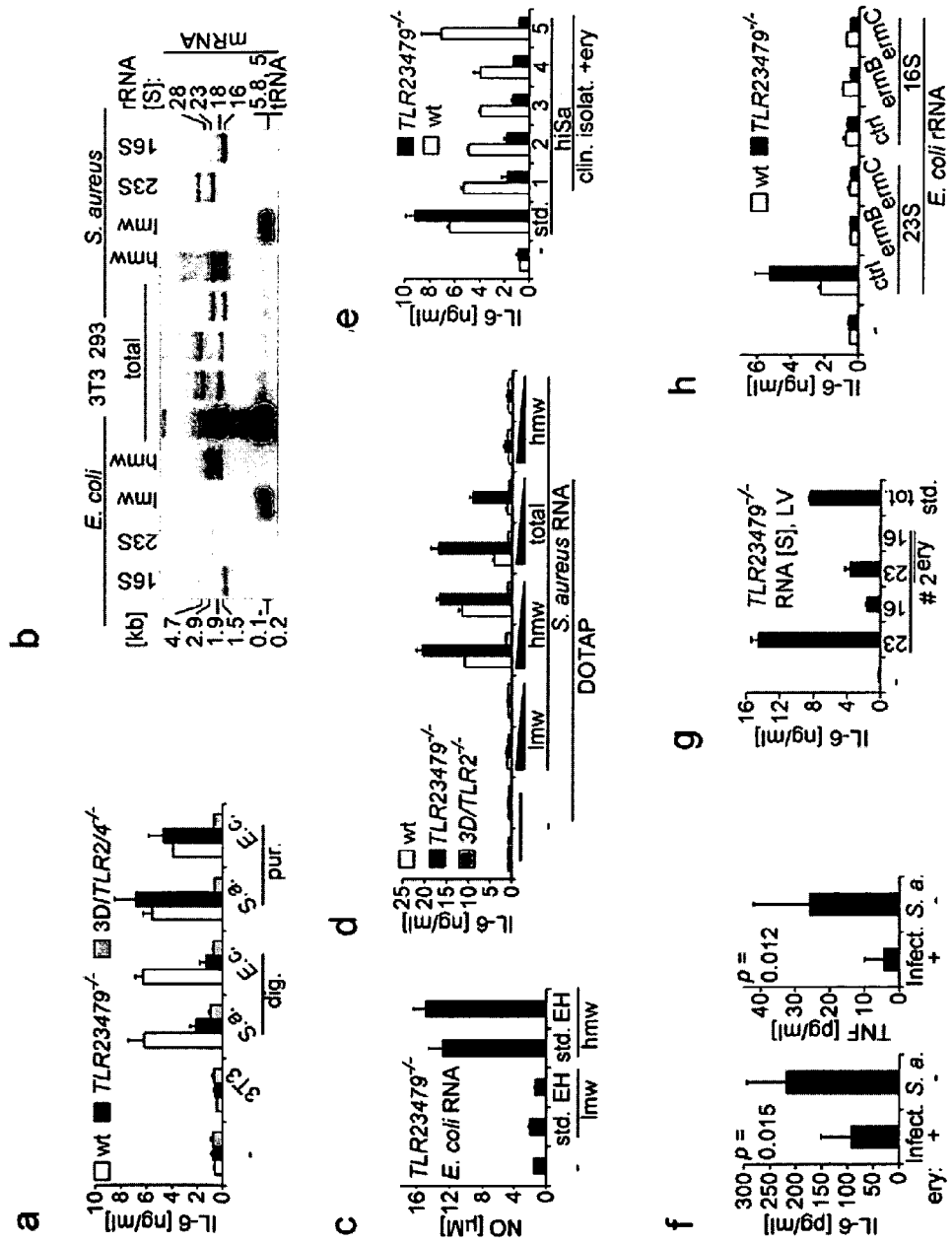

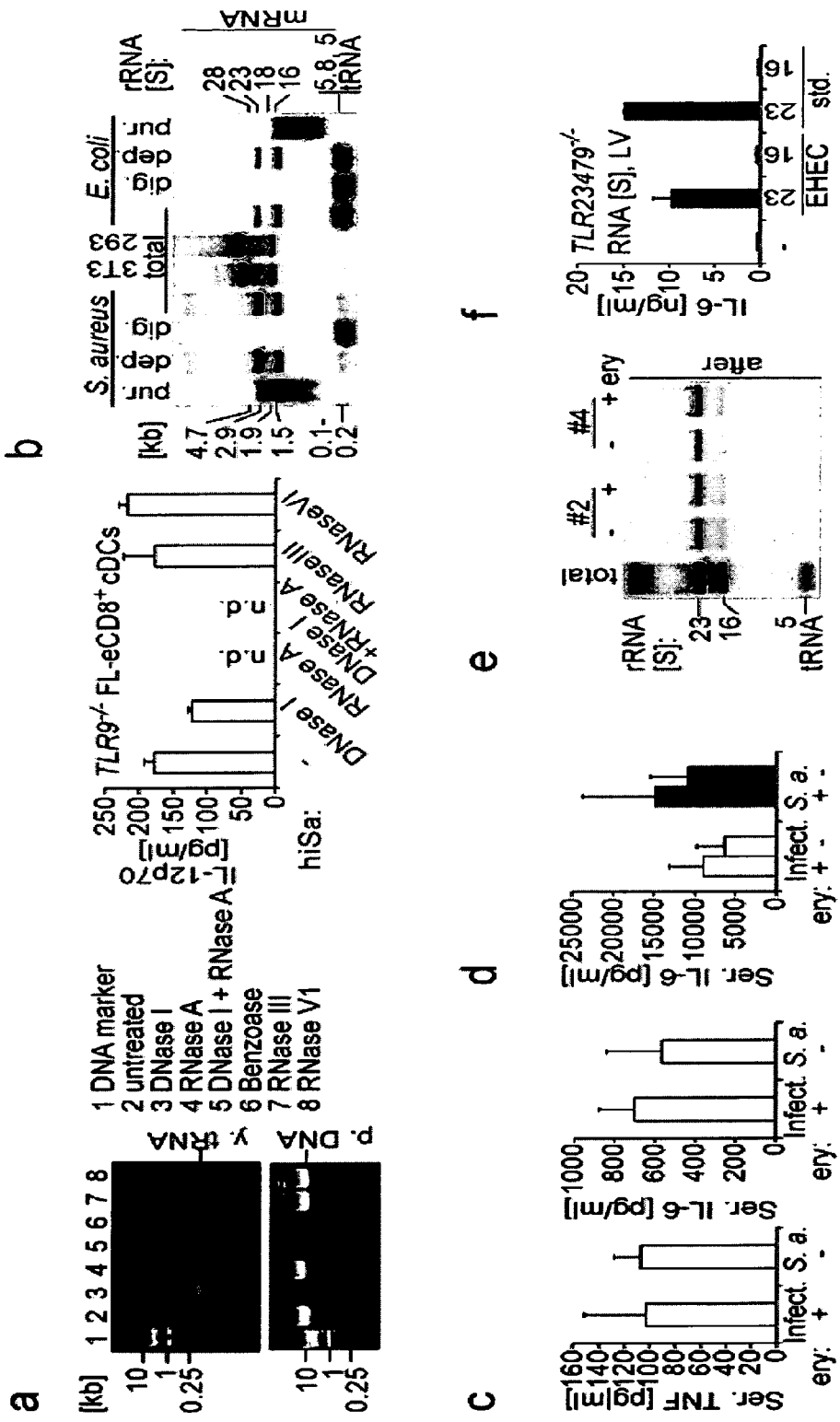
Figure 2.1

Figure 3:
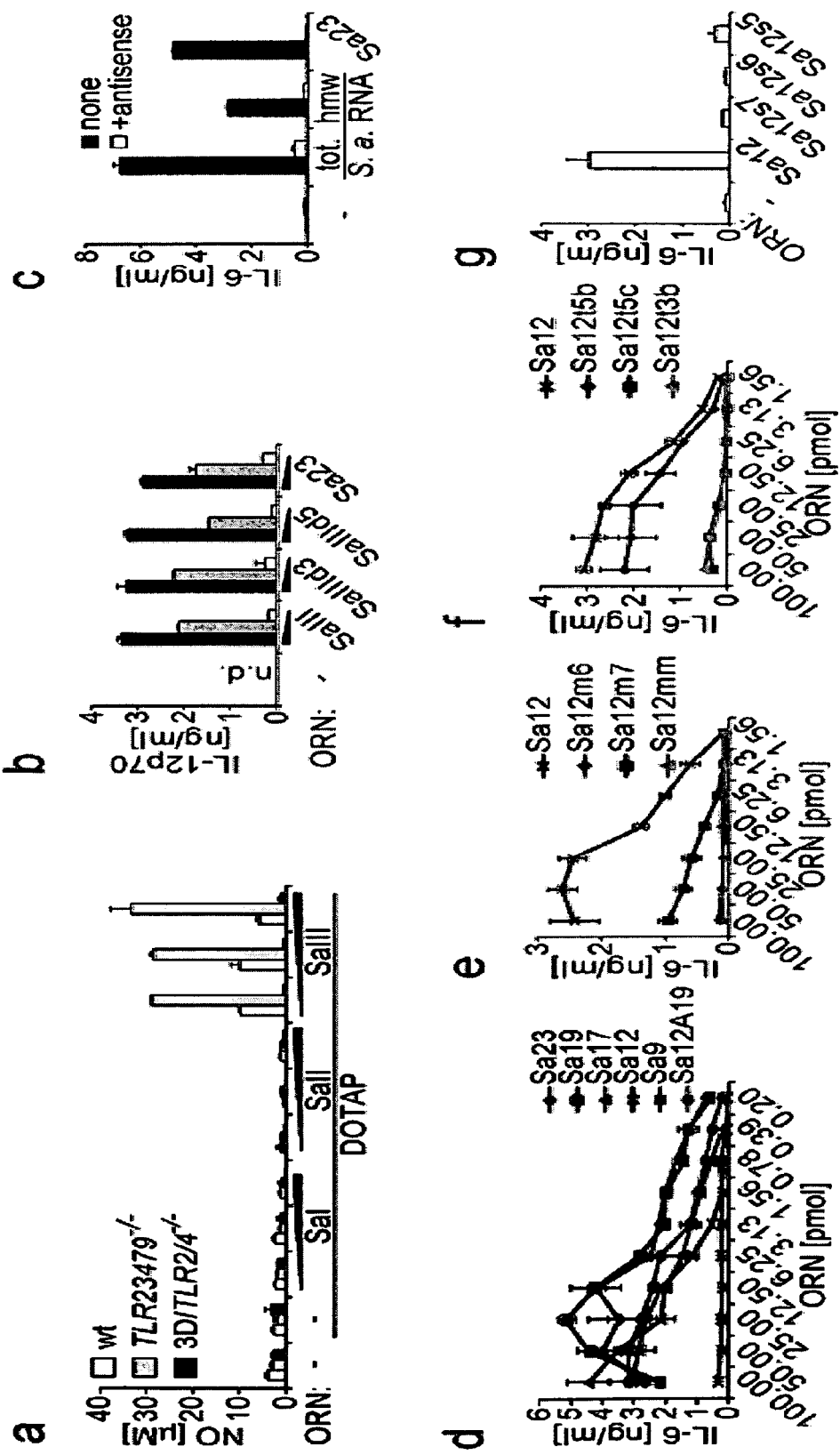

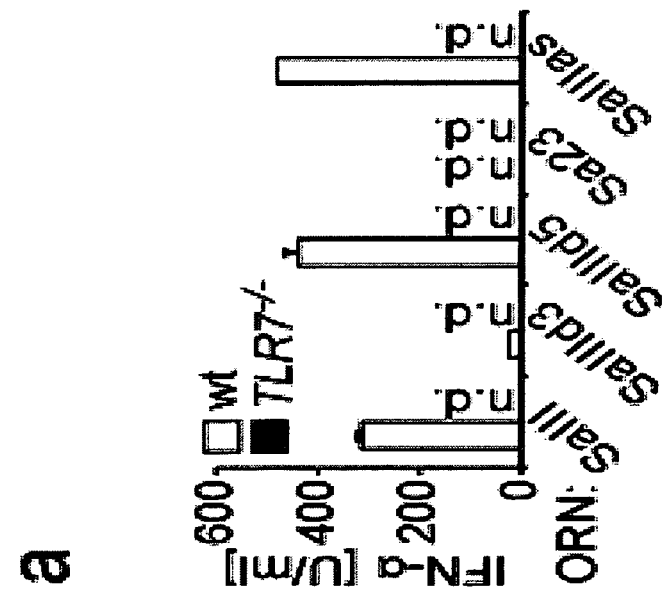
Figure 3.1

Figure 4:
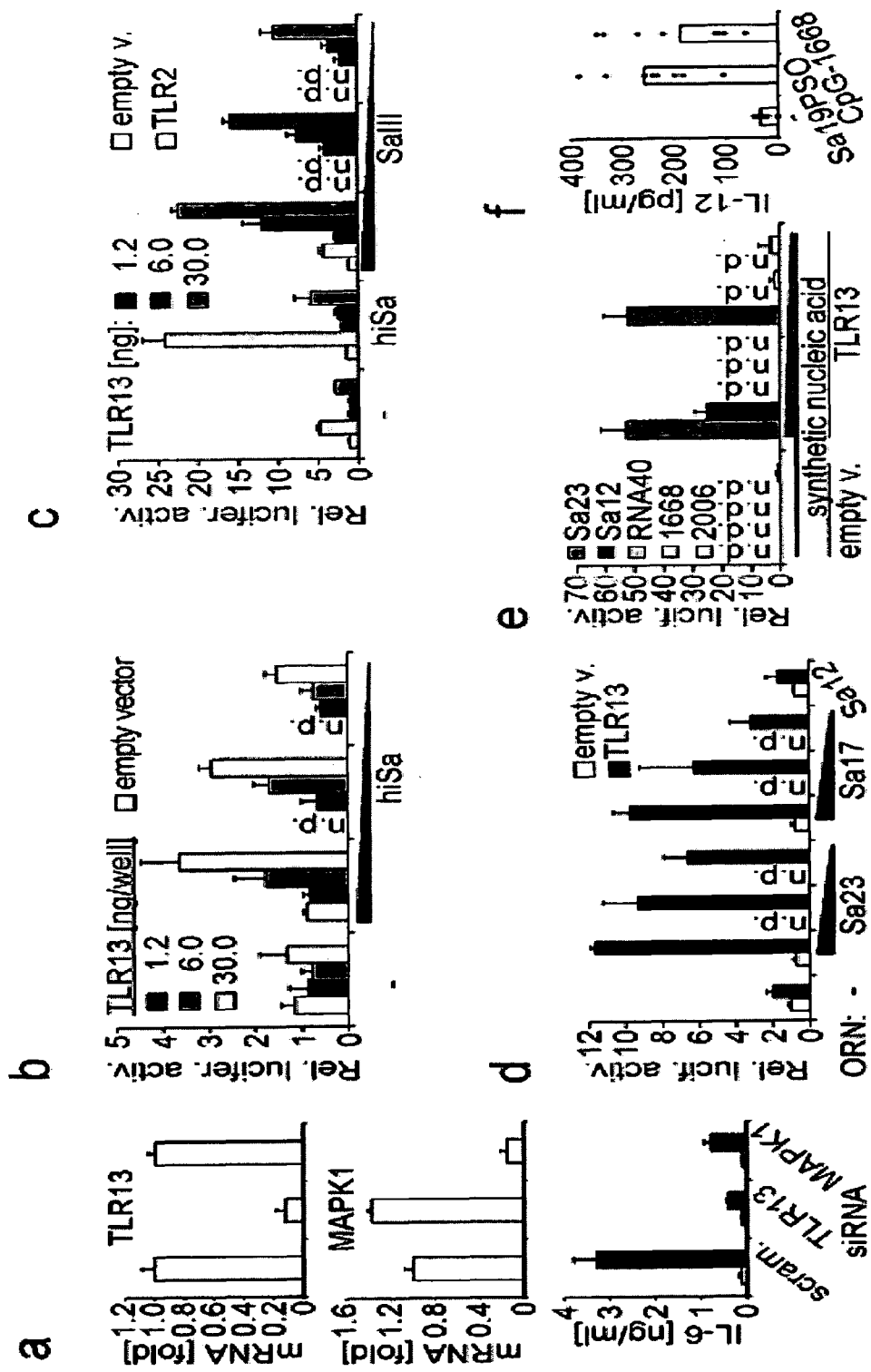

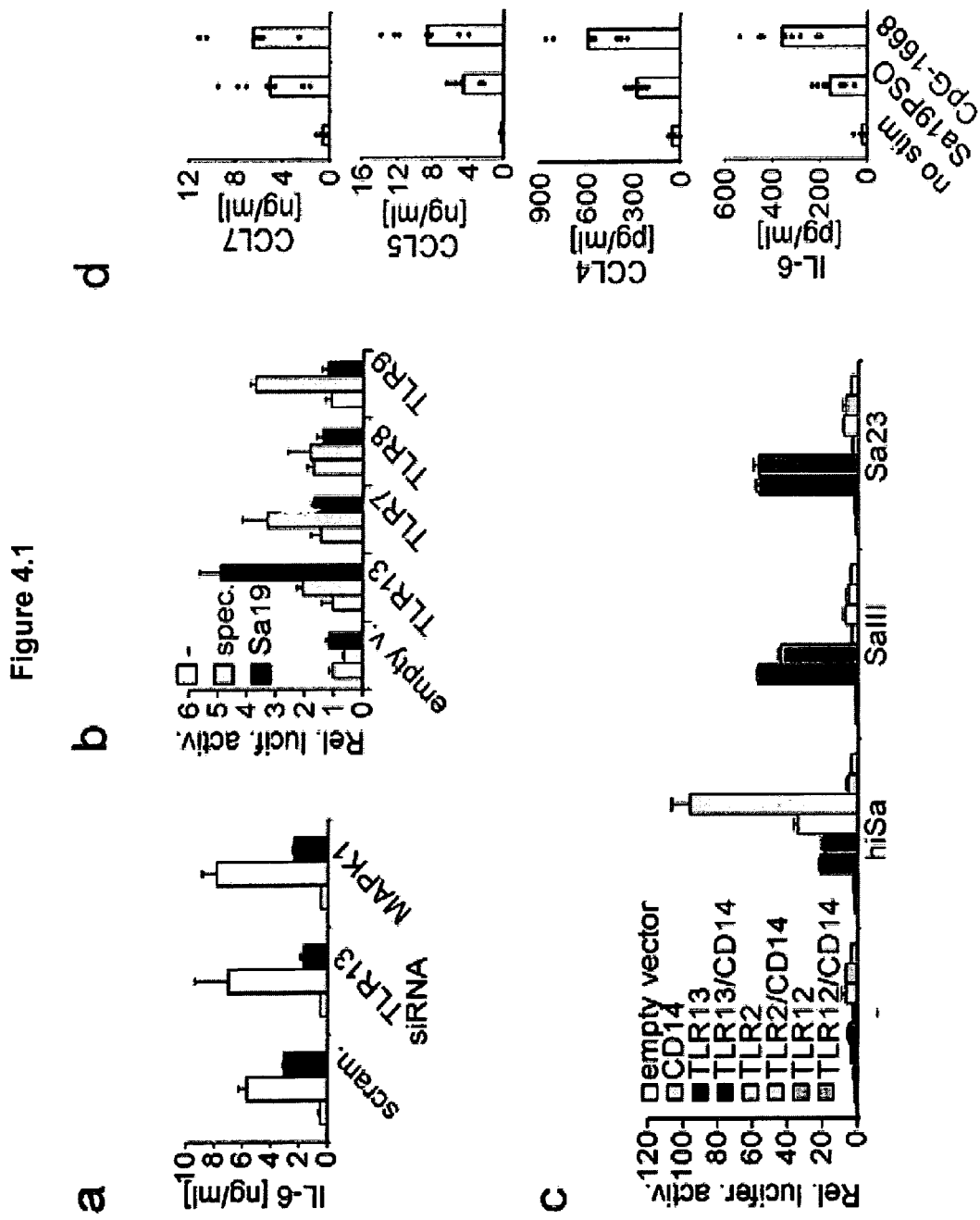
Figure 4.1

US 9,556,439 B2

AGONISTS AND ANTAGONISTS OF TOLL-LIKE RECEPTOR (TLR) 13

This application is a National Phase application under 35 U.S.C. §371 of International Application No. PCT/EP2013/00392, filed Feb. 8, 2013, and claims the benefit under 35 U.S.C. §119(e) of U.S. Provisional Patent Application 61/597,063 filed Feb. 9, 2012, the disclosure of which is incorporated by reference herein in its entirety.

FIELD OF THE INVENTION

The present invention relates to the field of immunology. The present invention provides agonists and antagonists of Toll-like receptor (TLR) 13. In particular, the present invention provides TLR13 activating and inhibiting nucleic acids, and provides such nucleic acids for use as pharmaceutical agents. The present invention further provides in vitro methods using such nucleic acids.

BACKGROUND OF THE INVENTION

The immune system recognises pathogens and potential danger with pattern recognition receptors (PRR). This sensing induces innate and adaptive immune responses and often is the prerequisite of a timely and effective immune defence against pathogens. However, an excessive immune response is dangerous and potential fatal as in the case of sepsis.

Among different families of PRR the Toll-like receptors (TLRs) have been recognized as very important for the activation of several innate and adaptive immune responses. Within the last years many different endogenous as well as artificial agonists and ligands for TLRs have been identified including agonists for TLR1, TLR2, TLR3, TLR4, TLR5, TLR6, TLR7, TLR8, TLR9, and TLR11. For example, certain viral RNA as the agonists for TLR7 and TLR8 have been identified[17]. This knowledge allowed the use of TLR-ligands as adjuvants for the induction of superior immune responses in vaccines or in different therapies against infectious diseases and cancer. On the other hand this knowledge made it possible to interfere with unwanted immune responses by blocking TLR recognition. Examples of unwanted or exaggerated immune responses are autoimmune diseases, infection and sepsis. The immune responses induced by different TLR-agonists differ greatly, thus the identification of new TLR-agonists allows a more fine tuned application, e.g. as adjuvants.

Whereas TLR2, TLR4 and TLR9 are major host sensors of Gram-negative bacteria, TLR2 and TLR7 are believed to be central detectors of Gram-positive bacteria.[1] Recognition of Gram-positive bacteria by TLR2 or TLR7 occurs via their lipoproteins, RNA and DNA, respectively[2-5]. However, the role of additional TLRs or other classes of PRRs such as C-type lectins, RIG-I-like helicases, or nucleotide binding domain- and leucine-rich repeat—containing proteins for detection of gram-positive bacteria is unclear. In particular, among the 13 different TLRs described in man and mouse the ligands for TLR10, TLR12 and TLR13 are unknown so far.

Thus, there is still a need for elucidating the role of TLRs in host protection from bacterial infection. In particular, it is an object to provide tools for targeting such TLRs, and methods and medical applications using them.

SUMMARY OF THE INVENTION

The object of the present invention is solved by a nucleic acid comprising or consisting of a sequence of SEQ ID NO: 1 (ACGGAAXXXCC) or a variant thereof for use as a pharmaceutical agent, where 'X' signifies any nucleotide (e.g., A, C, G, T, or U). In the appended Sequence listing 'X' is 'N' because of the prescribed WIPO ST.25 standard.

In one embodiment the nucleic acid comprises or consists of a sequence of SEQ ID NO: 2 (ACGGAAAGACC) or a variant thereof.

In one embodiment, the nucleic acid comprises or consists of a sequence selected from the group consisting of SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO) or a variant thereof.

In a preferred embodiment, the nucleic acid comprises or consists of a sequence of SEQ ID NO: 10 (Sa19PSO) or a variant thereof.

In one embodiment, the nucleic acid comprises or consists of SEQ ID NO: 11 (SaIII) or SEQ ID NO: 12 (SaIIId5) or a variant thereof.

In one embodiment, the nucleic acid is for use as a pharmaceutical agent for activating Toll-like receptor (TLR) 13 expressing cells in a subject.

In one embodiment, the nucleic acid is for use as a pharmaceutical agent for stimulating an immune response in a TLR13 expressing subject.

In one embodiment, the nucleic acid is for use as a pharmaceutical agent for (use in a method of) stimulating an immune response in a non-primate subject, preferably in a non-human subject.

In one embodiment, the pharmaceutical agent is an immunostimulant.

In one embodiment, the pharmaceutical agent is an adjuvant.

In a preferred embodiment, the adjuvant is for vaccination against bacterial infection. Also, in another preferred embodiment, the adjuvans is for use in a method for vaccination against bacterial infection.

In one embodiment, the pharmaceutical agent is for treating an infection by a Gram-positive or Gram-negative bacterium resistant to one or more antibiotics. Also, in another embodiment the pharmaceutical agent is for use in a method of treating an infection by a Gram-positive or Gram-negative bacterium resistant to one or more antibiotics In a preferred embodiment, the infection is a systemic or a local infection.

In another preferred embodiment, the Gram-positive or Gram-negative bacterium is resistant to one or more antibiotics of the macrolide, lincosamide, and streptogramin (MLS) group.

In a more preferred embodiment, the Gram-positive or Gram-negative bacterium is resistant to erythromycin.

In one embodiment, the Gram-positive bacterium is *Staphylococcus aureus* or *Streptococcus pneumoniae*.

The object of the present invention is further solved by a pharmaceutical composition comprising a nucleic acid comprising or consisting of a sequence of SEQ ID NO: 1 (ACGGAAXXXCC) or SEQ ID NO: 2 (ACGGAAAGACC) or a variant thereof.

In one embodiment, the pharmaceutical composition comprises a nucleic acid comprising or consisting of a sequence selected from the group consisting of SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), SEQ ID NO: 10 (Sa19PSO), SEQ ID NO: 11 (SaIII), and SEQ ID NO: 12

(SaIIId5) or a variant thereof, preferably comprising or consisting of a sequence of SEQ ID NO: 10 (Sa19PSO) or a variant thereof.

In one embodiment, the pharmaceutical composition is for systemic or local administration.

The object of the present invention is further solved by a nucleic acid comprising or consisting of a sequence of SEQ ID NO: 13 (UGCCUUXXXGG) or a variant thereof for use as a pharmaceutical agent.

In one embodiment, the nucleic acid comprises or consists of a sequence of SEQ ID NO: 14 (UGCCUUUCUGG) or a variant thereof.

In one embodiment, the nucleic acid comprises or consists of a sequence of SEQ ID NO: 15 (SaIIIas) or a variant thereof.

In one embodiment, the nucleic acid is for use as a pharmaceutical agent for inhibiting TLR13 expressing cells in a subject.

In one embodiment, the nucleic acid is for use as a pharmaceutical agent for inhibiting an immune response in a TLR13 expressing subject.

In one embodiment, the nucleic acid is for use as a pharmaceutical agent for inhibiting an immune response in a non-primate subject, preferably in a non-human subject.

In one embodiment, the pharmaceutical agent is an immunosuppressant.

In one embodiment, the pharmaceutical agent is for treating septic syndrome induced by bacteria.

In one embodiment, the pharmaceutical agent is for treating a local bacterial infection.

In a preferred embodiment, the pharmaceutical agent is a Gram-positive or Gram-negative bacterium.

In a preferred embodiment, the Gram-positive bacterium is *Staphylococcus aureus* or *Streptococcus pneumoniae*.

The object of the present invention is further solved by a pharmaceutical composition comprising a nucleic acid comprising or consisting of a sequence of SEQ ID NO: 13 (UGCCUUXXXGG) or SEQ ID NO: 14 (UGCCUUUCUGG) or a variant thereof.

In one embodiment, the pharmaceutical composition comprises a nucleic acid comprising or consisting of a sequence of SEQ ID NO: 15 (SaIIIas) or a variant thereof.

In one embodiment, the pharmaceutical composition is for systemic or local administration.

The object of the present invention is further solved by an in vitro method for activating TLR13 expressing cells, or for inducing cytokine and/or NO release from TLR13 expressing cells, comprising the step of contacting the cells with a nucleic acid comprising or consisting of a sequence of SEQ ID NO: 1 (ACGGAAXXXCC) or a variant thereof.

The object of the present invention is further solved by an in vitro method for studying TLR13 mediated cell activation, comprising the steps of:
(a) contacting TLR13 expressing cells, or cells to be examined for TLR13 expression, with a nucleic acid comprising or consisting of a sequence of SEQ ID NO: 1 (ACGGAAXXXCC) or a variant thereof;
(b) determining cytokine and/or NO release from the cells.

In one embodiment of the in vitro method for studying TLR13 medicated cell activation further comprises the step of contacting the cells with an inhibitor of TLR13 mediated cell activation prior to step (a).

In a preferred embodiment, the inhibitor is a nucleic acid comprising or consisting of an antisense sequence being complementary to the sequence of SEQ ID NO: 1 (ACGGAAXXXCC) or SEQ ID NO: 2 (ACGGAAAGACC) or a variant thereof.

In another preferred embodiment, the inhibitor is a nucleic acid comprising or consisting of an antisense sequence of SEQ ID NO: 13 (UGCCUUXXXGG) or SEQ ID NO: 14 (UGCCUUUCUGG) or a variant thereof.

In a more preferred embodiment, the inhibitor is a nucleic acid comprising or consisting of an antisense sequence of SEQ ID NO: 15 (SaIIIas) or a variant thereof.

In one embodiment of the above in vitro methods the nucleic acid comprises or consists of a sequence selected from the group consisting of SEQ ID NO: 2 (ACGGAAAGACC), SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO) or a variant thereof.

In one embodiment of the above in vitro methods the nucleic acid comprises or consists of SEQ ID NO: 11 (SaIII) or SEQ ID NO: 12 (SaIIId5) or a variant thereof.

In one embodiment of the above in vitro methods the cytokine is selected from the group consisting of IFN-λ, IL-6, IL-12p70, and TNFα.

In one embodiment of the above in vitro methods the TLR13 expressing cells are macrophages or conventional dendritic cells (cDCs).

In a preferred embodiment of the above in vitro methods the cytokine is IL-6 or TNFα, and the TLR13 expressing cells are macrophages.

In another preferred embodiment of the above in vitro methods the cytokine is IL-12p70, and the TLR13 expressing cells are cDCs.

In one embodiment of the above in vitro methods the cDCs are TLR23479$^{-/-}$ eCD8$^{high}$ cDCs or signal regulatory protein a (Sirp)$^{high}$ cDCs.

The object of the present invention is further solved by a use of a nucleic acid comprising or consisting of a sequence selected from the group consisting of a sequence of SEQ ID NO: 1 (ACGGAAXXXCC), SEQ ID NO: 2 (ACGGAAAGACC), SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO), SEQ ID NO: 11 (SaIII), SEQ ID NO: 12 (SaIIId5), SEQ ID NO: 13 (UGCCUUXXXGG), SEQ ID NO: 14 (UGCCUUUCUGG), and SEQ ID NO: 15 (SaIIIas) or a variant thereof for studying TLR13 expressing cells or TLR13 mediated signal transduction.

The object of the present invention is further solved by a nucleic acid comprising or consisting of a sequence selected from the group consisting of SEQ ID NO: 1 (ACGGAAXXXCC), SEQ ID NO: 2 (ACGGAAAGACC), SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO), SEQ ID NO: 11 (SaIII), SEQ ID NO: 12 (SaIIId5), SEQ ID NO: 13 (UGCCUUXXXGG), SEQ ID NO: 14 (UGCCUUUCUGG), and SEQ ID NO: 15 (SaIIIas) or a variant thereof.

The term "variant" of a defined nucleic acid means a nucleic acid being modified compared to the defined nucleic acid, e.g. in nucleotide sequence (e.g., by deletions, additions or exchanges/mutations/substitutions of nucleotides) or in individual nucleotides (e.g., by methylation of a nucleotide). In particular, the term shall include modifications of a defined nucleic acid aiming at stabilisation, e.g. by thioate or phosphorothioate modification. The term "variant" encompasses nucleic acids comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or more additional nucleotides compared to a nucleic acid of defined sequence (e.g., SEQ ID NO:2), nucleic acids comprising 1, 2, 3, 4, 5, or more fewer nucleotides compared to a nucleic acid of defined sequence (e.g., SEQ ID NO:2), nucleic acids comprising 1, 2, or more modified nucleotides (e.g., methylated nucleotides) compared to a nucleic acid of defined sequence (e.g., SEQ ID NO:2), and nucleic acids comprising 1, 2, 3, 4, 5, 6, 7, 8, or more nucleotide exchanges, mutations or substitutions compared to a nucleic acid of defined sequence (e.g., SEQ ID NO:2).

Preferably, a variant of SEQ ID NOs: 1-12, 16, 17, 18, or 19 is capable of activating Toll-like receptor (TLR) 13. Alternatively and/or additionally, it is preferred that a variant of SEQ ID NOs: 1-12, 16, 17, 18, or 19 is capable of activating TLR13 expressing cells. Alternatively and/or additionally, a variant of SEQ ID NOs: 1-12, 16, 17, 18, or 19 is capable of stimulating an immune response in a non-primate subject, preferably in a non-human subject.

TLR13 activation or inhibition, respectively; or activation or inhibition of TLR13 expressing cells, respectively, is preferably done by bringing macrophages or conventional dendritic cells (cDCs), preferably TLR23479$^{-/-}$ conventional dendritic cells (cDCs) or signal regulatory protein a (Sirp)$^{high}$ cDCs in contact with a nucleic acid or variant of the invention and determining the amount of cytokines, preferably IFN-λ, IL-6, IL-12p70, and/or TNFα, and/or NO produced from said cells in comparison to such cells that were not brought into contact with such a nucleic acid or variant in case activation should be tested. If the amount of cytokines and/or NO increases in cells brought into contact with a suspected or known TLR13 activating nucleic acid or variant in comparison to a cell that was not brought into contact, then the potential TLR13 activating nucleic acid or variant is activating TLR13. As a positive control which will result in cytokine and/or NO production, for example, the nucleic acid shown in SEQ ID NO: 2 may serve.

In case, inhibition is tested, macrophages or conventional dendritic cells (cDCs), preferably TLR23479$^{-/-}$ cDCs or signal regulatory protein a (Sirp)$^{high}$ cDCs are stimulated with a nucleic acid or variant of the invention that activates TLR13. Afterwards, macrophages or conventional dendritic cells (cDCs), preferably TLR23479$^{-/-}$ cDCs or signal regulatory protein α (Sirp)$^{high}$ cDCs are brought into contact with a nucleic acid or variant thereof suspected or known to inhibit TLR13 activation and the amount of cytokines and/or NO is determined. If the amount of cytokines and/or NO decreases in cells brought into contact with a potential TLR13 inhibiting nucleic acid or variant in comparison to a cell that was stimulated before, but is not brought into contact with a potential TLR13 inhibiting nucleic acid or variant, then the potential TLR13 inhibiting nucleic acid or variant is inhibiting TLR13.

Preferably, as a control for the specificity of the test TLR23479$^{-/-}$ pDCs that express TLR12 and lack TLR11, -13 may serve. These cells lack TLR-13 and, thus, are suitable to indicate as to whether any effect seen with TLR23479$^{-/-}$ cDCs is specific for TLR-13, since TLR23479$^{-/-}$ pDCs lack TLR-13 and thus, if they respond, then the nucleic acid or variant may not only be specific for TLR-13, but also for other TLRs, though this is not preferred.

Macrophages or conventional dendritic cells (cDCs), preferably TLR23479$^{-/-}$ cDCs and pDCs or signal regulatory protein a (Sirp)$^{high}$ cDCs may be obtained from mice lacking TLR2, 3, 4, 7, and 9. Such mice can be obtained by crossings. TLR23479$^{-/-}$ cDCs also express CD8$^{high}$ and TLR11, -12 and -13. The generation of cDCs and pDCs is described in documents 31 and 32.

As a negative control which will essentially not, preferably will not result in IL-6 and/or IL-12 production, for example, the nucleic acid shown in SEQ ID NO: 13

However, preferably, on the other hand a variant of SEQ ID NOs: 13, 14, or 15 is capable of inhibiting Toll-like receptor (TLR) 13. Alternatively and/or additionally, it is preferred that a variant of SEQ ID NOs: 13, 14, or 15 is capable of inhibiting TLR13 expressing cells. Alternatively and/or additionally, a variant of SEQ ID NOs: 13, 14, or 15 is capable of inhibiting an immune response in a non-primate subject, preferably in a non-human subject.

The term "immunostimulant" or "immunostimulator" or "immunostimulatory drug" or "immunostimulatory agent" means an agent that stimulates the immune system by inducing or increasing activity of any of its components. An immunostimulatory therapy may be considered for treating new-born or elderly subjects, or subjects otherwise having an immature immune system or impaired immune responses. An immunostimulatory therapy may also be indicated in the case of cancer.

The term "immunosuppressant" or "immunosuppressive drug" or "immunosuppressive agent" means an agent that inhibits or prevents activity of the immune system. An immunosuppressive therapy may be indicated in case of an excessive immune response, e.g. in septic syndrome, auto-immune diseases or allergies, or in order to prevent rejection of transplants.

The term "adjuvant" means an immunomodulatory agent, i.e. an immunostimulatory or immunosuppressive agent, which modifies the effect of other immunological agents. An adjuvant is often included in vaccines in order to enhance the recipient's immune response to the antigen. For example, an adjuvant enhancing the effect of another immunological agent may help keeping this immunological agent to a minimum.

DETAILED DESCRIPTION OF THE INVENTION

Here we have identified an ssRNA segment within the peptidyl transferase loop of bacterial 23S ribosomal (r) RNA that binds antibiotics of the MLS group as a ligand of the orphan receptor TLR13. In particular, we have shown by gene knockdown, gain of function experiments, as well as specific RNase treatments and fractionation of total bacterial RNA that TLR13 recognises the bacterial 23S rRNA segment "ACGGAAAGACC" (SEQ ID NO: 2).

Working with mice and murine immune cells it was found that certain Gram-positive bacteria, such as *Staphylococcus aureus* or *Streptococcus pneumoniae* were seen by immune cells even if other TLRs, previously described to be involved in the recognition of Gram-positive bacteria (TLR23479$^{-/-}$), were excluded. The stimulatory agent within Gram-positive bacteria was found to be sensitive to RNase treatment suggesting that RNA was the stimulatory component. Using different dendritic cell subsets, known to selectively express different combinations of TLR11, TLR12 and TLR13 allowed the identification of TLR13 as the PRR for the stimulatory RNA of Gram-positive bacteria. The separation of total RNA of Gram-positive bacteria identified ribosomal RNA as the stimulatory component. Synthetic RNA oligonucleotides from the 23S rRNA of bacteria down 12 base pairs lengths were highly stimulatory to TLR13. Certain methylations and base substitutions of those oligos abrogated TLR13.

Thus, the invention describes for the first time molecular natural as well as artificial agonists for the activation of TLR13. This allows using these agonists for the activation of immune responses via TLR13. This allows further the design of antagonists to inhibit unwanted TLR13 activation. Some exemplary TLR13 activating and inhibiting nucleic acids are shown in Table 1:

TABLE 1

*S. aureus* 23S rRNA mimicking and derived oligoribonucleotides (ORNs)

| Name | sequence | TLR7* | TLR13** |
|---|---|---|---|
| SaI: (SEQ ID NO: 33) | 5'-CCGACACAGGUAGUCAAGAU-3' | n.a. | − |
| SaII: (SEQ ID NO: 34) | GCACCUCGAΨGUCGC (Ψ, pseudouridine) | n.a. | − |
| SaIIIas: (SEQ ID NO: 15) | 3'-CCAAUGGGCGCUGUCCUGCCUUUCUGGGGCACCUCGAAAUGACAUCGG-5' | ++ | − |
| SaIII: (SEQ ID NO: 11) | 5'-GGUUACCCGCGACAGGACGGAAAGACCCCGUGGAGCUUUACUGUAGCC-3' | ++ | +++ |
| SaIIId3: (SEQ ID NO: 4) | GGUUACCCGCGACAGGACGGAAAGACCCCGUG | − | +++ |
| SaIIId5: (SEQ ID NO: 12) | GACGGAAAGACCCCGUGGAGCUUUACUGUAGCC | ++ | +++ |
| Sa23: (SEQ ID NO: 5) | CAGGACGGAAAGACCCCGUGGAG | − | +++ |
| Sa19: (SEQ ID NO: 6) | GGACGGAAAGACCCCGUGG | − | +++ |
| Sa17: (SEQ ID NO: 7) | GACGGAAAGACCCCGUG | − | +++ |
| Sa12: (SEQ ID NO: 8) | GACGGAAAGACC | − | +++ |
| Sa9: (SEQ ID NO: 20) | GGAAAGACC | − | − |
| Sa12s7: (SEQ ID NO: 21) | GACGGACAGACC | − | (+) |
| Sa12s6: (SEQ ID NO: 22) | GACGGGAAGACC | − | − |
| Sa12s5: (SEQ ID NO: 23) | GACGAAAGACC | − | (+) |
| Sa12st: (SEQ ID NO: 24) | AAAAGAAAGAAA | − | − |
| Sa12t3a: (SEQ ID NO: 25) | GACGGAAAGAAA | − | + |
| Sa12t5a: (SEQ ID NO: 26) | AAAAGAAAGACC | − | (+) |
| Sa12t3b: (SEQ ID NO: 27) | GACGGAAAGACA | − | + |
| Sa12t5b: (SEQ ID NO: 3) | AACGGAAAGACC | − | +++ |
| Sa12t5c: (SEQ ID NO: 28) | AAAGGAAAGACC | − | + |
| Sa12sec: (SEQ ID NO: 29) | GACCCAAAGAGG | − | − |
| Sa12m6: (SEQ ID NO: 30) | GACGGAAAGACC (with m modifications) | − | − |

TABLE 1 -continued

S. aureus 23S rRNA mimicking and derived oligoribonucleotides (ORNs)

| Name | sequence | TLR7* | TLR13** |
|---|---|---|---|
| Sa12m7: (SEQ ID NO: 31) | GACGGAAAGACC | − | ++ |
| Sa12mm: (SEQ ID NO: 32) | mm GACGG*A*AAGACC | − | − |
| Sa12A19: (SEQ ID NO: 9) | AAACGGAAAGACCAAAAAA | − | +++ |
| Sa19PSO: (SEQ ID NO: 10) | GGACGGAAAGACCCCGUGG | − | +++ |

*IFN-α from wt-FL-pDCs upon challenge with 100 pmol ORN (+ Lyovec) per well
**IL-6 [pg/ml] from total wt-BM cells upon challenge with 100 pmol ORN + LV/well;
−, <100;
(+), 100-199,
+, 200-499;
++, 500-1999;
+++, >2000;
n.a., not analyzed;
bold, position of A that is methylated within total 23S rRNA;
italics, mutated or methylated;
PSO/underlined, stabilized by thioate modification.

In more detail, a TLR13 activating minimal nucleic acid sequence is as follows:

(ACGGAAXXXCC), SEQ ID NO: 1
or (ACGGAAAGACC) SEQ ID NO: 2

Nucleic acid sequences found to activate TLR13 are as shown in Table 1:
SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), or SEQ ID NO: 10 (Sa19PSO)

Nucleic acid sequences found to activate both TLR13 and TLR7 are as shown in Table 1:
SEQ ID NO: 11 (SaIII) or SEQ ID NO: 12 (SaIIId5)
A TLR13 inhibiting nucleic acid is as follows:

(UGCCUUXXXGG), SEQ ID NO: 13
or (UGCCUUUCUGG) SEQ ID NO: 14

A TLR13 inhibiting nucleic acid found to inhibit TLR13 is as shown in Table 1:
SEQ ID NO: 15 (SaIIIas).
Further TLR13 activating nucleic acid sequences are as follows:

(GCCGGAAAGACC; Sa12s2), SEQ ID NO: 16

(GACGGAACGACC; Sa12s8), SEQ ID NO: 17

(GACGGAAAAACC; Sa12s9), SEQ ID NO: 18
or (GACGAAAGCCC; Sa12s10) SEQ ID NO: 19

A nucleic acid of the present invention is preferably in an 'isolated' form. The term "isolated" as used herein in the context of a nucleic acid refers to removal of the nucleic acid from its natural source, environment or milieu.

The present invention may also be characterized by the following items:
(1) A nucleic acid comprising or consisting of a sequence of SEQ ID NO: 1 (ACGGAAXXXCC) or a variant thereof for use as a pharmaceutical agent.
(2) The nucleic acid according to item 1, comprising or consisting of a sequence of SEQ ID NO: 2 (ACGGAAAGACC) or a variant thereof.
(3) The nucleic acid according to item 1 or 2, comprising or consisting of a sequence selected from the group consisting of SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO) or a variant thereof.
(4) The nucleic acid according to item 3, comprising or consisting of a sequence of SEQ ID NO: 10 (Sa19PSO) or a variant thereof.
(5) The nucleic acid according to item 1 or 2, comprising or consisting of SEQ ID NO: 11 (SaIII) or SEQ ID NO: 12 (SaIIId5) or a variant thereof.
(6) The nucleic acid according to any of the preceding items for use as a pharmaceutical agent for activating Toll-like receptor (TLR) 13 expressing cells in a subject.
(7) The nucleic acid according to any of the preceding items, wherein the pharmaceutical agent is an immunostimulant.
(8) The nucleic acid according to any of the preceding items, wherein the pharmaceutical agent is an adjuvant, preferably for vaccination against bacterial infection.
(9) The nucleic acid according to any of the preceding items for use as a pharmaceutical agent for treating an infection by a Gram-positive or Gram-negative bacterium resistant to one or more antibiotics, preferably resistant to one or more antibiotics of the macrolide, lincosamide, and streptogramin (MLS) group, most preferably resistant to erythromycin.

(10) The nucleic acid according to item 9, wherein the Gram-positive bacterium is *Staphylococcus aureus* or *Streptococcus pneumoniae*.

(11) A pharmaceutical composition comprising a nucleic acid comprising or consisting of a sequence of SEQ ID NO: 1 (ACGGAAXXXCC) or SEQ ID NO: 2 (ACGGAAAGACC) or a variant thereof.

(12) The pharmaceutical composition according to item 11, comprising a nucleic acid comprising or consisting of a sequence selected from the group consisting of SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), SEQ ID NO: 10 (Sa19PSO), SEQ ID NO: 11 (SaIII), and SEQ ID NO: 12 (SaIIId5) or a variant thereof, preferably comprising or consisting of a sequence of SEQ ID NO: 10 (Sa19PSO) or a variant thereof.

(13) A nucleic acid comprising or consisting of a sequence of SEQ ID NO: 13 (UGCCUUXXXGG) or a variant thereof for use as a pharmaceutical agent.

(14) The nucleic acid comprising or consisting of a sequence of SEQ ID NO: 14 (UGCCUUUCUGG) or a variant.

(15) The nucleic acid according to item 13 or 14, comprising or consisting of a sequence of SEQ ID NO: 15 (SaIIIas) or a variant thereof.

(16) The nucleic acid according to any of items 13 to 15 for use as a pharmaceutical agent for inhibiting TLR13 expressing cells in a subject.

(17) The nucleic acid according to any of items 13 to 16, wherein the pharmaceutical agent is an immunosuppressant.

(18) The nucleic acid according to any of items 13 to 17, for use as a pharmaceutical agent for treating septic syndrome induced by a Gram-positive or Gram-negative bacterium.

(19) The nucleic acid according to item 18, wherein the Gram-positive bacterium is *Staphylococcus aureus* or *Streptococcus pneumoniae*.

(20) A pharmaceutical composition comprising a nucleic acid comprising or consisting of a sequence of SEQ ID NO: 13 (UGCCUUXXXGG) or SEQ ID NO: 14 (UGCCUUUCUGG) or a variant thereof.

(21) The pharmaceutical composition according to item 20, comprising a nucleic acid comprising or consisting of a sequence of SEQ ID NO: 15 (SaIIIas) or a variant thereof.

(22) An in vitro method for activating TLR13 expressing cells, or for inducing cytokine and/or NO release from TLR13 expressing cells, comprising the step of contacting the cells with a nucleic acid comprising or consisting of a sequence of SEQ ID NO: 1 (ACGGAAXXXCC) or a variant thereof.

(23) An in vitro method for studying TLR13 mediated cell activation, comprising the steps of:
(c) contacting TLR13 expressing cells, or cells to be examined for TLR13 expression, with a nucleic acid comprising or consisting of a sequence of SEQ ID NO: 1 (ACGGAAXXXCC) or a variant thereof;
(d) determining cytokine and/or NO release from the cells.

(24) The in vitro method according to item 23, further comprising the step of contacting the cells with an inhibitor of TLR13 mediated cell activation prior to step (a), preferably with an antisense oligonucleotide comprising or consisting of a sequence of SEQ ID NO: 13 (UGCCUUXXXGG) or SEQ ID NO: 14 (UGCCUUUCUGG) or a variant thereof, most preferably comprising or consisting of a sequence of SEQ ID NO: 15 (SaIIIas) or a variant thereof.

(25) The in vitro method according to any of items 22 to 24, wherein the nucleic acid comprises or consists of a sequence selected from the group consisting of SEQ ID NO: 2 (ACGGAAAGACC), SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO) or a variant thereof.

(26) The in vitro method according to any of items 22 or 25, wherein the nucleic acid comprises or consists of SEQ ID NO: 11 (SaIII) or SEQ ID NO: 12 (SaIIId5) or a variant thereof.

(27). The in vitro method according to any of items 22 to 26, wherein the cytokine is selected from the group consisting of IFN-λ, IL-6, IL-12p70, and TNFα.

(28) The in vitro method according to any of items 22 to 26, wherein the TLR13 expressing cells are macrophages or conventional dendritic cells (cDCs).

(29) The in vitro method according to item 28, wherein the cDCs are TLR23479$^{-/-}$ eCD8$^{high}$ cDCs or signal regulatory protein α (Sirp)$^{high}$ cDCs.

(30) Use of a nucleic acid comprising or consisting of a sequence selected from the group consisting of a sequence of SEQ ID NO: 1 (ACGGAAXXXCC), SEQ ID NO: 2 (ACGGAAAGACC), SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO), SEQ ID NO: 11 (SaIII), SEQ ID NO: 12 (SaIIId5), SEQ ID NO: 13 (UGCCUUXXXGG), SEQ ID NO: 14 (UGCCUUUCUGG), and SEQ ID NO: 15 (SaIIIas) or a variant thereof for studying TLR13 expressing cells or TLR13 mediated signal transduction.

(31) A nucleic acid comprising or consisting of a sequence selected from the group consisting of SEQ ID NO: 1 (ACGGAAXXXCC), SEQ ID NO: 3 (Sa12t5b), SEQ ID NO: 4 (SaIIId3), SEQ ID NO: 5 (Sa23), SEQ ID NO: 6 (Sa19), SEQ ID NO: 7 (Sa17), SEQ ID NO: 8 (Sa12), SEQ ID NO: 9 (Sa12A19), and SEQ ID NO: 10 (Sa19PSO), SEQ ID NO: 11 (SaIII), SEQ ID NO: 12 (SaIIId5), SEQ ID NO: 13 (UGCCUUXXXGG), SEQ ID NO: 14 (UGCCUUUCUGG), and SEQ ID NO: 15 (SaIIIas) or a variant thereof.

In the following, the present invention will be described in more detail on the basis of the examples and with reference to the accompanying figures, in which FIG. 1 shows that Gram-positive bacteria activate TLR23479$^{-/-}$ macrophages and DCs via MyD88.

a, b, c, e, wt and k. o. macrophages were preincubated in 20 μg/ml of a TLR2 neutralizing antibody (if indicated) and challenged with 10$^9$ (rectangle) and 10$^8$, as well as 10$^7$ and 10$^6$ cfu/ml (indicated by triangles) of heat inactivated *S. aureus* (hiSa, titered prior to inactivation). Culture supernatants were sampled and analyzed by ELISA. a, Results of wt macrophages challenge with 10$^9$ cfu/ml hiSa was set to 100% (representing 2 to 10 ng/ml) to which the other concentrations within the respective block were related (challenge for 8 h). b, Macrophages were preincubated for 30 min with dimethyl sulfoxide (DMSO) alone or with 50 nM bafilomycin A before 8 h microbial challenge. c, Macrophages were challenged for 16 h. d, Mice were challenged intravenously (i. v.) with 10$^9$ cfu hiSa. Serum samples were analyzed by ELISA (the data are representative for 3 experiments, each group with n=3 mice). e-g, The indicated hiSa suspensions have been preincubated with RNase A (+) prior to challenge of macrophages (e, f) or DCs (g) for 16 h (e, g) or times indicated (f, lysates were subjected to SDS PAGE and immunoblot analysis); P, phosphorylated. g, Flt3-ligand (FL)-derived DC subsets were challenged for 16 h and the cytokine contents of the supernatants were analyzed. The respective TLR expression (expr.) in DC subset equivalents is indicated (hi, high; −, no detectable expression; +, expression).

FIG. 1.1 shows that Gram-positive bacteria activate 3D macrophages unless TLR2 is blocked.

Macrophages were pre-incubated with 20 μg/ml of a neutralizing antibody (a) towards TLR2 if indicated and were challenged with $10^9$, $10^8$, and $10^7$ cfu/ml heat inactivated S. aureus (hiSa, triangles), which was either untreated or pre-treated with RNaseA. Supernatants were sampled 16 h later and analyzed by ELISA.

FIG. 2 shows that bacterial 23S rRNA is stimulatory unless its A2085/2058 is methylated.

a, c, d, e, g, h, After challenge of macrophages for 16 h, supernatants were sampled for cytokine or nitrite (NO) content. a, Bacterial RNA preparations resulting from incubation of total RNAs with 5′-phosphate-specific exo RNase targeting large rRNAs (dig.) or precipitation of both large rRNAs (pur.) were applied to macrophages. b, Bacterial RNA together with eukaryotic cell line RNA preparations were gel-electrophoresed analytically (kb, kilo bases; S, Svedberg; r, ribosomal; t, transfer; m, messenger). b-d, Bacterial total RNAs were separated by anion-exchange chromatography into low molecular weight (lmw) and high molecular weight (hmw) fractions, or by agarose gel electrophoresis after which 16S and 23S rRNA-containing gel slices were cut out and RNA was re-isolated and subsequently transfected into macrophages (std., regular E. coli isolate; EH, enterohemorrhagic E. coli). e, Erythromycin (ery) resistant clinical S. aureus isolates (clin. isolat.) were cultured in 10 mg/l erythromycin (+ery). Macrophages were challenged with $10^9$ cfu/ml heat inactivated erythtromycin sensitive (std.) or -resistant (numbered from 1 to 5) S. aureus (hiSa). f, TLR23479$^{-/-}$ mice (n=6) were infected (Infect.) intravenously with logarithmically growing $10^8$ cfu erythromycin resistant S. aureus (S. a.) clinical isolate that had been grown in the presence (+) or absence (−) of erythromycin. Serum was drawn after 2 h and analyzed for cytokines by cytometric bead array. g, Next, 23S (23) or 16S (16) rRNA, or total (tot.) RNA preparations from numbered clinical isolate (#2) or control (std.) S. aureus grown in the presence of erythromycin (ery) or in its absence were transfected with lyovec (LV). h, E. coli BL21 was transformed with erythromycin resistance methyltransferase (erm) B or C expression plasmids or not (ctrl, control) and cultured. Large rRNAs were isolated and transfected into macrophages.

FIG. 2.1 shows that single-stranded bacterial 23S RNA activates TLR23479$^{-/-}$ macrophages.

a, Yeast (y.) tRNA and plasmid (p.) DNA were treated with the indicated nucleases as control and applied to an agarose gel. Heat-inactivated S. aureus (hiSa) bacteria were nuclease treated as indicated and FL-DCs were challenged with $10^7$ cfu/ml nuclease- or PBS-treated (−) hiSa for 16 h. b, Total bacterial RNAs were incubated with 5′-phosphate-specific exo RNase targeting large rRNAs (dig.), 5′phosphate-specific phosphatase (dep.), or subjected to precipitation of both large rRNAs (pur.; kb, kilo bases; S, Svedberg; r, ribosomal; t, transfer; m, messenger). c, wt mice (n=6) were infected with $10^8$ cfu logarithmically growing clinical erythromycin-resistant S. aureus (S. a.) isolate cultured in the presence (+) or absence (−) of erythromycin (ery). Serum was drawn 2 h after infection and analyzed by CBA. d, Infection was performed as described in b 16 h upon which serum was drawn (white columns, wt; black columns, TLR23479$^{-/-}$; n=6 for each genotype). e, Agarose gels carrying isolated 23S rRNA fractions isolated from total RNA of resistant S. aureus (#, number of isolate) grown in the presence (+) or absence (−) of erythromycin (ery). f, Macrophages were transfected with Lyovec (LV) for 16 h with large rRNA fractions from entero-hemorrhagic E. coli (EHEC) or regular clinical isolate (std.) E. coli.

FIG. 3 shows that ORNs harbouring the 23S rRNA sequence around A2085/2058 activate macrophages and cDCs.

a-g, Cells were challenged for 16 h. Thereafter supernatants were assayed for proinflammatory cytokine contents. a, Sequence motifs covering 3 separate methylation sites in S. aureus 23S rRNA were mirrored by ORNs (see sequences in Table 1), which were transfected into macrophages. b, TLR23479$^{-/-}$ FL-eCD8$^+$ cDCs were transfected with the ORNs indicated (amount/well [pmol]: black, 10; grey, 1; white, 0.1). c, TLR23479$^{-/-}$ Sirp$^{high}$ cDCs were transfected with the S. aureus RNA preparations indicated or an ORN covering the SaIII core sequence (10 pmol/well), either in the absence (none) of or upon preincubation for 20 min with 100 pmol/well antisense RNA ORN (SaIIIas, +antisense). d,-g, Bone marrow cells were challenged with transfected ORNs at doses indicated (or 100 pmol/well if not indicated).

FIG. 3.1 shows that TLR13-activating ORNs additionally activate TLR7, and specific mutations abrogate TLR13 activation.

a, b, FL-pDCs of the genotypes indicated (a) and wt bone marrow cells (b) were challenged with 100 pmol/well ORNs by transfection (Lyovec) for 16 h.

FIG. 4 shows that TLR13 recognises heat-inactivated S. aureus and ORNs mirroring bacterial 23S rRNA segments covering A2085/2058.

a, Macrophages were transfected with siRNAs to knock down specific mRNA accumulation (MAPK1, ERK2) or with control siRNA (scram., upper diagrams). Upon transfection cells were seeded and left untreated (white columns in lower diagram), or challenged with 100 pmol/well ORN SaIII (black columns) for 16 h. Supernatants were analyzed by ELISA. b-e, Human embryonic kidney (HEK) 293 line cells were transfected with TLR expression and luciferase reporter plasmids. After 24 h they were challenged for 16 h to analyze NF-κB driven relative (rel.) luciferase (lucifer. or lucif.) activity (activ.); n.d., not detectable; n.p., not performed; v., vector; −, no challenge. b, c, With varying doses or one dose of TLR expression plasmid (TLR2: 2 ng) or empty (30 ng) vector transfected cells were challenged with $10^9$ (no indication, c) or additionally $10^8$ and $10^7$ cfu/ml of heat-inactivated S. aureus (hiSa, triangle, b), or 100 (d, e) or 10, or 1 pmol/well ODN (triangle, c-e). d, e, 15 ng/well TLR13 expression plasmid was transfected. e, Either 10 μM of CpG-DNA only, or additionally 1 μM of CpG-DNA (triangle) was applied. ORNs and CpG-DNA were transfected with DOTAP. f, Next, 10 nmol of ORN or CpG-DNA were given i. v. into mice (n=9). Serum was drawn 6 h later from challenged and untreated mice (−) for analysis by cytometric bead arrays (IL-12, IL-12p70).

FIG. 4.1 shows that specifically TLR13 mediates cellular and systemic recognition of the 23S rRNA segment that encompasses A2085/2058.

a, Macrophages were transfected with siRNAs specific for the mRNA molecules indicated (MAPK1, ERK2) or control siRNA (scram.). After transfection, cells were seeded and left untreated (white columns) or challenged for 16 h with $10^8$ or $10^7$ cfu/ml heat inactivated *S. aureus* (hiSa; light grey or dark grey columns, respectively). b, c, Human embryonic kidney (HEK) 293 cells were transfected for 24 h with plasmids for expression of pattern recognition receptors (PRRs) as indicated or with empty vector (v.) and NF-κB reporter plasmid upon which cells were challenged for 16 h and lysed to analyze relative (rel.) luciferase (lucifer. or lucif.) activity (activ.). b, Cells were left untreated (−), challenged with individual stimuli (spec.; TLR13: $10^8$ cfu/ml hiSa; TLR7: 4 µg/ml CL075; TLR8: $10^8$ cfu/ml hiSa; TLR9: 2 µM CpG-1668) or transfected with 100 pmol/well Sa10 by Lyovec. c, Cells were left untreated (−) or challenged with $10^8$ cfu/ml hiSa or 100 pmol/well of ORNs indicated. d, Mice were challenged by i. v. injection of 10 nmol of ORN or CpG-DNA (n=9). Serum was drawn 6 h later from treated and untreated (no stim) mice for analysis of cytokine content by cytometric bead array.

EXAMPLES

Materials and Methods

Materials. RNase free DNase I (Roche), RNaseH (Fermentas), DNase I and RNaseA (Sigma), RNaseIII (NEB), and RNaseVI (Ambion) were applied according to supplier indications. Cells were preincubated with anti TLR2 antibody[9] (clone T2.5, HBT) and bafilomycin A (Sigma) used as blockers. Anti phospho-ERK1/2 and -p38 (cell signaling) and anti alpha actinin (Santa Cruz) antibodies were used for immuno blot analysis. ORNs (IBA or Metabion) as well as CpG DNA-1668 and -2006 (TIB-Molbiol) were in aqueous solutions. Dotap (Roche) and lyovec (Invivogen) were used for transfections.

Bacteria. *S. aureus* (DSMZ 20231), *B. subtilis* (DSMZ 10), and *S. pneumoniae* (D39), as well as clinical isolates of *E. coli*[9] including EHEC O104:H4 and *S. aureus* were used for challenges in vivo or in vitro, or as sources of RNA preparations used for cell transfection (1 µg total RNA or 0.2 µg RNA fraction per well of a 96 well plate using lyovec normally). For bacteria preparation and erythromycin conditioning, bacteria were cultured in the absence or presence of 10 µg/ml erythromycin and were inoculated with 16 h grown preparatory cultures (agitation, 37° C., *E. coli* in LB medium, *S. aureus*, *B. subtilis*, and *S. pneumoniae* in BHI, the latter in $CO_2$ incubator). In the logarithmic phases of main cultures, which were delayed by erythromycin for 40 min, bacteria were pelleted and collected in PBS for RNA preparation, heat inactivation (incubation in boiling water for 15 min), or infection. Bacterial samples (taken prior to inactivation) were always titered[9].

Mice. CARD9$^{-/-}$, RIP2$^{-/-}$, ASC$^{-/-}$, IL-1R1$^{-/-}$, and IL-18$^{-/-}$ mice were bred at the animal facility of the Institute of Medical Microbiology, Immunology, and Hygiene, Technical University of Munich. Wt C57BL/6, TLR23479$^{-/-}$ and single TLR k. o. mice[15], 3D[13] (acquired from MMRC of the Scripps Research Institute) from which 3D/TLR2$^{-/-}$ and 3D/TLR2/4$^{-/-}$ were derived by cross breeding, as well as MyD88$^{-/-}$[1] mice were used as sources of in vitro generated DC subpopulations and macrophages. Challenged mice were anaesthetized by short incubation in an isoflurane saturated glass barrel. Thereupon blood was sampled by retrobulbar dotting. Animal experiments were approved by local authorities.

Cells and Challenges. Macrophages and DCs were derived from bone marrow cells while HEK293 cells were grown as cell line[26,27]. FL-DCs were generated, FACS sorted, stimulated in the presence of IL-12p70 promoting cytokines, and challenged. Thereafter supernatant cytokine amounts were determined[27]. Total bone marrow cells were transfected with ORNs. Thereafter IL-6 was analysed by ELISA.

RNA Preparations. Bacterial RNAs were prepared by acidic phenol extraction[28]. Briefly, bacteria were washed and solubilised in 50 nM sodium azide, raised in glass milk (ribolyzer, MPbio), extracted, and precipitated. 1% agarose gels using MOPS running buffer were applied for RNA analysis and fractionation. The 16S and 23S rRNAs were dephosphorylated with RNA 5'-polyphosphatase and digested with terminator 5'-phosphate-dependent exonuclease (both from Epicentre Biotechnologies). The Microbeexpress bacterial mRNA enrichment kit (Ambion) including 16/23S rRNA complementary DNA coupled to magnetic beads was used to purify both of the two large rRNAs together. Lmw and hmw fractions were isolated from total RNA by anion-exchange chromatography using nucleobond RNA/DNA 400 columns (Macherey-Nagel) while total RNA was separated on a preparative agarose gel from which slices were cut out that contained 16S or 23S rRNA which subsequently were purified (Zymoclean gel RNA recovery kit, Zymoresearch). For RT PCR analysis of mRNA expression macrophages were opened up by 2 min panning in phenol solution (trifast, Peqlab). Upon addition of chloroform (Roth) the aqueous was separated from the organic phase by centrifugation and RNA precipitated for 16 h at 4° C., washed in ethanol and resuspended in water by incubation at 55° C. for 10 min.

Cytokine and NO Measurement. ELISA (R&D) and CBA (e-bioscience) was as described[9,27]. Nitrite was quantified according to the Griess protocol to indicate cellular NO release. Briefly, 0.2% N-(1-naphtyl) ethylene diamine dihydrochloride was mixed with 2% sulphanilamide in 5% phosphoric acid (all Sigma) as 1:1 (by volume). This mixture was mixed with cell culture supernatant as 1:1 (by volume). Resultant absorption at 540 nm was determined immediately to calculate nitrite concentration by comparison to a sodium nitrite (Sigma) standard reference curve.

Phosphorylation Analysis. Lysate analysis by immuno blotting was as described[9].

Erm Overexpression. Total RNA was isolated from a clinical erythromycin-resistant *S. aureus* isolate growing in 10 µg/ml erythromycin (logarithmic phase). The ermC cds was amplified by RT PCR and subcloned (sequenced). The ermB cds was subcloned from a Gram-positive bacteria expression vector pat18[29] (also used to exchange ermB cds by that of ermC to both transform into *B. subtilis*). Both cdss were ligated into the Gram-negative bacteria expression vector pGEX2T (GE lifesciences). Constructs were transformed into *E. coli* strain BL21 codon plus (Stratagene) for conference of erythromycin resistance.

mRNA Knock Down. Macrophages were generated by incubation of bone marrow cells in teflon foil bags (Sarstedt No. 94.6077.317)[30]. siRNA (Qiagen) towards murine TLR13 mRNA (ID SI01449518) and MAPK1/ERK2 mRNA (ID 1022564, positive control), as well as a scrambled variant (ID 1027310, negative control) were transfected by electroporation (gene pulser Biorad, exponential protocol, 400 V, 150 µF, 100Ω) in optimem medium (Invitrogen). 48 h later cells were challenged for 16 h. Supernatants were analyzed by ELISA and Griess assay and RNA was isolated from cells (s. above). RNA was DNase I (Roche) digested, oligo dT18 primed and reversely transcribed (M-MuLv, Fermentas). DNA amplification by RT PCR (maxima sybr green/rox, Fermentas) was monitored (7500 Fast, Applied Biosystems). Threshold cycle (CT) was determined for each sample and related to respective actin sample value. Results for treated were related to those of respective untreated samples to calculate fold mRNA expression (2-ΔΔCT).

Luciferase Assay. Murine TLR12 and TLR13 (Invivogen) or other PRR expression plasmids were transfected together with luciferase reporter plasmids into HEK293 cells for analysis of NF-κB driven and constitutive luciferase activities, as previously described[26].

Statistics. Students t-test for unconnected samples was applied to calculate significances.

Example 1

Identification of TLR13 as a Single-Stranded (ss) RNA Sensor

We compared macrophages lacking the expression of caspase recruitment domain (CARD) 9 (CARD9$^{-/-}$), receptor-interacting protein 2 (RIP2$^{-/-}$), apoptosis-associated speck-like protein containing a CARD (ASC$^{-/-}$), IL-1 receptor 1 (IL-1R$^{-/-}$), IL-18 (IL-18$^{-/-}$), or MyD88 (MyD88$^{-/-}$) in terms of their responsiveness to heat-inactivated S. aureus (hiSa) or S. pneumoniae in the presence of a TLR2-blocking antibody (αTLR2)[1,8-12]. Cytokine production was found to be strictly dependent on MyD88 (FIG. 1a), a finding that implies the involvement of MyD88-dependent TLRs.

Next we asked whether endosomal TLRs (TLR3, -7, -8, -9, -11, and -13) are involved in cell activation. We inhibited endosomal acidification with bafilomycin and analyzed UNC93B1-defective (3D) macrophages that lack ER—endosome TLR trafficking[1,13,14]. Blocking of endosomal acidification abrogated recognition of Gram-positive bacteria in TLR2$^{-/-}$ macrophages (FIG. 1b). Furthermore, 3D macrophages (or mice) lacking additionally TLR2 and -4 were unresponsive to bacterial challenge (FIG. 1c, d; FIG. 1.1). However, TLR23479$^{-/-}$ macrophages or mice[15] responded well to hiSa challenge unless the bacterial preparations were subjected to RNaseA treatment (FIG. 1e, f). Thus, hiSa was recognized by immune cells even if other TLRs, previously described to be involved in the recognition of Gram-positive bacteria (TLR23479$^{-/-}$), were excluded.

Dendritic cell (DC) subsets express different sets of TLRs[16]. We generated equivalents (e) of in vivo conventional (c) DC (known to express TLR13) and plasmacytoid (p) DC (lacking TLR13 expression) in vitro with flt3-ligand (FL). The responsiveness of these cells to hiSa was dependent on MyD88 and 3D. Specifically, TLR23479$^{-/-}$ eCD8$^{high}$ and signal regulatory protein α (Sirp)$^{high}$ cDCs responded to hiSa, whereas TLR23479$^{-/-}$ pDCs failed to do so (FIG. 1g).

Together, these findings indicate that TLR13 may be a bacterial single-stranded (ss) RNA sensor.

Example 2

Identification of 23S rRNA as the Stimulatory ssRNA

To identify the relevant RNA, we incubated hiSa with DNAse I, calf intestinal phosphatase, 5'-phosphate-specific phosphatase (to affect the integrity of 16S and 23S rRNA), or double-stranded (ds) RNA-specific RNase III or VI. These treatments did not alter the stimulatory activity of hiSa, in line with a recent report (FIG. 2.1a, b)[18]. However, nucleic acid-degrading benzonase and ssRNA-specific RNaseA abrogated the TLR23479$^{-/-}$ cDC and macrophage stimulatory activity of hiSa (FIG. 1e, f, g; FIG. 2.1a).

We then treated total RNA with 5"-phosphate-dependent exonuclease and precipitated large rRNAs (FIG. 2.1b) to narrow down the stimulatory activity. After transfection, 16S/23S rRNA isolates of both S. aureus and E. coli triggered the activation of TLR23479$^{-/-}$ macrophages and cDCs while 16S/23S rRNA digestion abrogated stimulatory activity (FIG. 2a). Whereas low molecular weight (lmw) portions from total RNA lacked a stimulatory activity, high molecular weight (hmw) portions of Gram-negative and Gram-positive bacterial RNA activated TLR23479$^{-/-}$ cells (FIG. 2b-d). These findings suggested that a fraction of large bacterial rRNAs activates macrophages and cDCs in a MyD88-dependent manner.

Because modification of bacterial rRNA, such as by the methyltransferases ermB or ermC, confers resistance to antibiotics such as erythromycin[7,19], we analyzed five clinical S. aureus isolates displaying various resistance phenotypes, including erythromycin resistance. When these isolates were grown in the presence of erythromycin, they largely lacked the capacity to immediately activate TLR23479$^{-/-}$ mice and pure macrophages, whereas wild-type (wt) control responses were normal (FIG. 2e, f; FIG. 2.1c, d). In contrast, all erythromycin-resistant S. aureus isolates grown in the absence of erythromycin strongly stimulated TLR23479$^{-/-}$ mice and cells (FIG. 2f). These results suggested an erythromycin-driven RNA camouflage from its receptor.

Accordingly and also in line with erythromycin-mediated N6 mono- or di-methylation of 23S rRNA adenosine (A) 2085 (corresponding to E. coli A2058, leading to resistance towards MLS antibiotics)[6,7], 23S rRNA from S. aureus grown in erythromycin was hardly stimulatory. In contrast, 23S rRNA from resistant S. aureus not grown in erythromycin and also from E. coli (including EHEC) but not 16S rRNA of both activated TLR23479$^{-/-}$ macrophages to normal degrees (FIG. 2g; FIG. 2.1e, f). Moreover, overexpression of ermB and ermC (the latter being subcloned from cDNA of an erythromycin grown S. aureus isolate) conferred in E. coli and B. subtilis strains erythromycin resistance and ablated 23S rRNA stimulatory activity towards TLR23479$^{-/-}$ macrophages (FIG. 2h). These data indicated that resistance to MLS group antibiotics (including erythromycin) mediated by site-specific methylation (targeting A2085 in S. aureus and A2058 in E. coli 23S rRNA) rendered 23S rRNA non-stimulatory.

Example 3

Identification of the Minimal Stimulatory Sequence

To address the immune stimulatory activity of 23S rRNA in more detail, we designed three ORNs as analogues of S. aureus 23S rRNA segments each of which carries an A in its centre that becomes methylated constitutively or under growth restriction to modulate the docking of protein synthesis cofactors or antibiotics. The three ORNs named SaI, SaII, and SaIII represented S. aureus A1662 (E. coli A1616, methylation of which promotes fitness[20]), S. aureus A2530 (E. coli A2503, targeted by chloramphenicol, florfenicol, and clindamycin resistance RNA methyltransferase[21]), as well as S. aureus A2085[6,7] (E. coli A2058), respectively (Table 1).

Only SaIII (which mirrors S. aureus A2085) activated TLR23479$^{-/-}$ cells (FIG. 3a). PDCs recognised SaIII via TLR7, but this activity was lost with 3'-terminal deletion (FIG. 3.1a). ORNs resulting from deletions of 3'- and 5'-termini (SaIIId3, SaIIId5, Sa23) equally activated TLR23479$^{-/-}$ cDCs (FIG. 3b), whereas preincubation of S. aureus RNA or of ORN Sa23 with an antisense SaIII RNA strand (SaIIIas) abrogated the stimulatory activity (FIG. 3c). These results indicated single strand structure as well as singularity of the stimulatory activity within the bacterial transcriptome.

Successive terminal deletions towards a 12-mer ORN (Sa12, Table 1) led to sequences that are identical in S. aureus and E. coli 23S rRNAs. Length dependent reduction of stimulatory capacity could largely be compensated by terminal fill-ups (Sa12A19, FIG. 3d)[22]. Sa12 N6-methylated at A6 (corresponding to S. aureus A2085 and mimicking erm-methylated 23S rRNA) lacked stimulatory capacity, whereas A7 N6-methylation merely caused partial reduction (FIG. 3e). Mutations at the termini of Sa12 revealed "ACG-GAAAGACC" (SEQ ID NO: 35) as the minimal stimulatory segment (Sa12t5b) because further mutation of the 5' end (Sa12t5c) or the 3' end (Sa12t3b) abrogated the stimulatory activity (FIG. 3f; FIG. 3.1.b; Table 1).

Coincidentally, the macrolide, lincosamide, and streptogramin (MLS)-group antibiotics (such as erythromycin) binding site is contained in this motif that carries A2085 in S. aureus (or A2058 in E. coli) 23S rRNA, the N6 methylation or mutation of which confers resistance to MLS antibiotics[6,7]. Hence, 23S rRNA from clinical isolates of erythromycin-resistant S. aureus and from erythromcin resistance methyltransferase (erm) B/C overexpressing bacteria, as well as synthetic oligoribonucleotides (ORNs) carrying N6 methylated A or a guanosine (G) as A2085/2058 replacements failed to stimulate TLR13. Our results thus demonstrate that sequence-specific 23S rRNA modifications render bacteria resistant to certain naturally occurring antibiotics and to immune recognition by TLR13.

On the other hand, Sa12 derivatives mimicking eukaryotic 28S rRNA or specific 23S rRNA mutations that render bacteria resistant to MLS antibiotics (S. aureus 23S rRNA A2085G, mimicked by A6G/Sa12s6) failed to stimulate bone marrow cells (FIG. 3g, Table 1)[7,19,23]. These findings suggested that molecular mechanisms rendering bacteria resistant to naturally occurring antibiotics also impede MyD88 dependent host recognition by an ill-defined endosomal TLR.

In addition, our data unravel an unanticipated link between antibiotic resistance and evasion from TLR13 recognition, since 23S rRNA modifications generating resistance towards MLS antibiotics also camouflaged bacteria from TLR13 recognition. MLS antibiotics producing bacteria such as Saccharopolyspora erythraea were possibly first to express erms (to resist their own antibiotics)[6]. Erm expression plasmids might have been acquired from S. erythraea by staphylococci, pneumococci, and mycobacteria[6,24]. As resistance trait spinoff, the pathogenic recipients gained invisibility to TLR13. We therefore speculate that widespread ancient antibiotic resistance[25] has subverted TLR13 driven antibacterial immune resistance. This may explain why TLR13 expression has been abandoned in certain mammalian species, including human.

Example 4

A TLR8$^{-/-}$ cell analysis ruled out the involvement of TLR8 (not shown). We thus focussed at TLR13-specific siRNA-driven suppression of TLR13 mRNA accumulation that impaired the recognition of hiSa or stimulatory ORNs such as SaIII (FIG. 1g; FIG. 4a; FIG. 4.1a). Furthermore, ectopic expression of TLR13 but not of CD14, TLR3, -7, -8, -9 or -12 conferred to HEK293 cell responsiveness towards challenge with hiSa or the ORNs SaIII, Sa23, Sa17, or Sa12 (FIG. 4b-d; FIG. 4.1b, c). Other nucleotides such as RNA40 (TLR7 ligand) or CpG-DNA (TLR9 ligand) were inactive (FIG. 4e). In vivo application of a phosphorothioate Sa19 variant (Sa19PSO) triggered systemic pro-inflammatory cytokine release similar to that elicited by the PSO-CpG-oligodeoxynucleotide 1668 (FIG. 4f; FIG. 4.1d).

REFERENCES

1 Kawai, T. & Akira, S. Toll-like receptors and their crosstalk with other innate receptors in infection and immunity. *Immunity* 34, 637-650 (2011).
2 Brightbill, H. D. et al. Host defense mechanisms triggered by microbial lipoproteins through toll-like receptors. *Science* 285, 732-736. (1999).
3 Hemmi, H. et al. A Toll-like receptor recognizes bacterial DNA. *Nature* 408, 740-745. (2000).
4 Karikó, K., Buckstein, M., Ni, H. & Weissman, D. Suppression of RNA recognition by Toll-like receptors: the impact of nucleoside modification and the evolutionary origin of RNA. *Immunity* 23, 165-175 (2005).
5 Mancuso, G. et al. Bacterial recognition by TLR7 in the lysosomes of conventional dendritic cells. *Nat Immunol* 10, 587-594 (2009).
6 Skinner, R. H. & Cundliffe, E. Dimethylation of adenine and the resistance of *Streptomyces erythraeus* to erythromycin. *J Gen Microbiol* 128, 2411-2416 (1982).
7 Weisblum, B. Erythromycin resistance by ribosome modification. *Antimicrob Agents Chemother* 39, 577-585 (1995).
8 Girardin, S. E. et al. Nod2 is a general sensor of peptidoglycan through muramyl dipeptide (MDP) detection. *J Biol Chem* 278, 8869-8872 (2003).
9 Spiller, S. et al. TLR4-induced IFN-gamma production increases TLR2 sensitivity and drives Gram-negative sepsis in mice. *J Exp Med* 205, 1747-1754 (2008).
10 Ruland, J. CARD9 signaling in the innate immune response. *Ann N Y Acad Sci* 1143, 35-44 (2008).
11 Muñoz-Planillo, R., Franchi, L., Miller, L. S. & Núñiez, G. A critical role for hemolysins and bacterial lipoproteins in *Staphylococcus aureus*-induced activation of the NIrp3 inflammasome. *J Immunol* 183, 3942-3948 (2009).
12 Tschopp, J. & Schroder, K. NLRP3 inflammasome activation: The convergence of multiple signalling pathways on ROS production? *Nat Rev Immunol* 10, 210-215 (2010).
13 Blasius, A. L. & Beutler, B. Intracellular toll-like receptors. *Immunity* 32, 305-315 (2010).
14 Brinkmann, M. M. et al. The interaction between the ER membrane protein UNC93B and TLR3, 7, and 9 is crucial for TLR signaling. *J Cell Biol* 177, 265-275 (2007).
15 Conrad, M. L. et al. Maternal TLR signaling is required for prenatal asthma protection by the nonpathogenic microbe *Acinetobacter lwoffii* F78. *J Exp Med* 206, 2869-2877 (2009).
16 Luber, C. A. et al. Quantitative proteomics reveals subset-specific viral recognition in dendritic cells. *Immunity* 32, 279-289 (2010).
17 Heil, F. et al. Species-specific recognition of single stranded RNA via Toll-like receptor 7 and 8. *Science* 303, 1526-1529 (2004).
18 Deshmukh, S. D. et al. Macrophages recognize streptocci through bacterial single-stranded RNA. *EMBO Rep* 12, 71-76 (2011).

19 Vester, B. & Douthwaite, S. Macrolide resistance conferred by base substitutions in 23S rRNA. *Antimicrob Agents Chemother* 45, 1-12 (2001).
20 Sergiev. P. V., Serebrvakova, M. V., Bogdanov, A. A. & Dontsova, O. A. The ybiN gene of *Escherichia coli* encodes adenine-N6 methyltransferase specific for modification of A1618 of 23 S ribosomal RNA, a methylated residue located close to the ribosomal exit tunnel. *J Mol Biol* 375, 291-300 (2008).
21 Long, K. S., Poehlsgaard, J., Kehrenberg, C., Schwarz, S. & Vester, B. The Cfr rRNA methyltransferase confers resistance to Phenicols, Lincosamides, Oxazolidinones, Pleuromutilins, and Streptogramin A antibiotics. *Antimicrob Agents Chemother* 50, 2500-2505 (2006).
22 Hornung, V. et al. Sequence-specific potent induction of IFN-alpha by short interfering RNA in plasmacytoid dendritic cells through TLR7. *Nat Med* 11, 263-270 (2005).
23 Klinge, S., Voigts-Hoffmann, F., Leibundgut, M., Arpagaus, S. & Ban, N. Crystal structure of the eukaryotic 60S ribosomal subunit in complex with initiation factor 6. *Science* 334, 941-948 (2011).
24 Buriánková, K. et al. Molecular basis of intrinsic macrolide resistance in the *Mycobacterium tuberculosis* complex. *Antimicrob Agents Chemother* 48, 143-150 (2004).
25 D'Costa, V. M. et al. Antibiotic resistance is ancient. *Nature* 477, 457-461 (2011).
26 Spiller, S. et al. Cellular recognition of trimyristoylated peptide or enterobacterial lipopolysaccharide via both TLR2 and TLR4. *J Biol Chem* 282, 13190-13198 (2007).
27 Lauterbach, H. et al. Mouse CD8alpha+ DCs and human BDCA3+ DCs are major producers of IFN-lambda in response to poly IC. *J Exp Med* 207, 2703-2717 (2010).
28 Fuchs, S., Pané-Farré, J., Kohler, C., Hecker, M. & Engelmann, S. Anaerobic gene expression in *Staphylococcus aureus*. *J Bacteria* 189, 4275-4289 (2007).
29 Trieu-Cuot, P., Carlier, C., Poyart-Salmeron, C. & Courvalin, P. Shuttle vectors containing a multiple cloning site and a lacZ alpha gene for conjugal transfer of DNA from *Escherichia coli* to gram-positive bacteria. *Gene* 102, 99-104 (1991).
30 Wiese, M. et al. Small interfering RNA (siRNA) delivery into murine bone marrow-derived macrophages by electroporation. *J Immunol Methods* 353, 102-110 (2010).
31 Fancke B, Suter M, Hochrein H, O'Keeffe M. M-CSF: a novel plasmacytoid and conventional dendritic cell poietin. *Blood*. 2008 Jan. 1; 111(1):150-9.
32 Vremec D, O'Keeffe M, Hochrein H, Fuchsberger M, Caminschi I, Lahoud M, Shortman K. Production of interferons by dendritic cells, plasmacytoid cells, natural killer cells, and interferon-producing killer dendritic cells. *Blood*. 2007 Feb. 1; 109(3):1165-73.

The invention claimed is:

1. A method for modulating Toll-like receptor-13 (TLR-13) or Toll-like receptor-13 (TLR-13)-expressing cells in a subject, comprising: administering to the subject a pharmaceutical agent comprising SEQ ID NO:1, SEQ ID NO: 13, SEQ ID NO:15, or a functional variant thereof, wherein the functional variant thereof is capable of: (1) activating TLR-13; (2) activating TLR-13 expressing cells; or (3) is capable of stimulating an immune response in a non-primate subject.

2. The method of claim 1, wherein modulating Toll-like receptor-13 (TLR-13) or Toll-like receptor-13 (TLR-13)-expressing cells comprises activating Toll-like receptor-13 (TLR-13) or Toll-like receptor-13 (TLR-13)-expressing cells.

3. The method of claim 1, wherein modulating Toll-like receptor-13 (TLR-13) or Toll-like receptor-13 (TLR-13)-expressing cells comprises inhibiting Toll-like receptor-13 (TLR-13) or Toll-like receptor-13 (TLR-13)-expressing cells.

4. The method of claim 1, wherein the functional variant of SEQ ID NO:1 is selected from SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO:12.

5. The method of claim 1, wherein the functional variant of SEQ ID NO: 13 is SEQ ID NO: 14.

6. A method for modulating Toll-like receptor-13 (TLR-13) or Toll-like receptor-13 (TLR-13)-expressing cells in a subject, comprising: administering to the subject a pharmaceutical agent comprising SEQ ID NO:1, SEQ ID NO: 13, SEQ ID NO: 15.

* * * * *

SEQUENCE LISTING

```
<160> NUMBER OF SEQ ID NOS: 35

<210> SEQ ID NO 1
<211> LENGTH: 11
<212> TYPE: RNA
<213> ORGANISM: Artificial
<220> FEATURE:
<223> OTHER INFORMATION: TLR13 activating minimal nucleid acid sequence
<220> FEATURE:
<221> NAME/KEY: misc_feature
<222> LOCATION: (7)..(9)
<223> OTHER INFORMATION: n =a, t, g or c
<220> FEATURE:
<221> NAME/KEY: misc_feature
<222> LOCATION: (7)..(9)
<223> OTHER INFORMATION: n =a, u, g or c

<400> SEQUENCE: 1
acggaannnc c                                                          11

<210> SEQ ID NO 2
<211> LENGTH: 11
<212> TYPE: RNA
<213> ORGANISM: Artificial
<220> FEATURE:
<223> OTHER INFORMATION: TLR13 activating minimal nucleid acid sequence

<400> SEQUENCE: 2
acggaaagac c                                                          11

<210> SEQ ID NO 3
<211> LENGTH: 12
<212> TYPE: RNA
<213> ORGANISM: Artificial
<220> FEATURE:
<223> OTHER INFORMATION: TLR13 activating nucleid acid sequence
<220> FEATURE:
<221> NAME/KEY: misc_feature
<222> LOCATION: (1)..(1)
<223> OTHER INFORMATION: Mutated
```

```
<220> FEATURE:
<221> NAME/KEY: misc_feature
<222> LOCATION: (6)..(6)
<223> OTHER INFORMATION: Position of A that is methylated within total
      23 S rRNA

<400> SEQUENCE: 3
aacggaaaga cc                                                              12

<210> SEQ ID NO 4
<211> LENGTH: 32
<212> TYPE: RNA
<213> ORGANISM: Artificial
<220> FEATURE:
<223> OTHER INFORMATION: TLR13 activating sequence
<220> FEATURE:
<221> NAME/KEY: misc_feature
<222> LOCATION: (21)..(21)
<223> OTHER INFORMATION: position of A that is methylated within total
      23S rRNA

<400> SEQUENCE: 4
gguuacccgc gacaggacgg aaagaccccg ug                                        32

<210> SEQ ID NO 5
<211> LENGTH: 23
<212> TYPE: RNA
<213> ORGANISM: Artificial
<220> FEATURE:
<223> OTHER INFORMATION: Nucleid acid sequence activating TLR13
<220> FEATURE:
<221> NAME/KEY: misc_feature
<222> LOCATION: (9)..(9)
<223> OTHER INFORMATION: position of A that is methylated within total
      23S rRNA

<400> SEQUENCE: 5
caggacggaa agaccccgug gag                                                  23

<210> SEQ ID NO 6
<211> LENGTH: 19
<212> TYPE: RNA
<213> ORGANISM: Artificial
<220> FEATURE:
<223> OTHER INFORMATION: Nucleid acid activating TLR 13
<220> FEATURE:
<221> NAME/KEY: misc_feature
<222> LOCATION: (7)..(7)
<223> OTHER INFORMATION: position of A methylated within total 23S rRNA

<400> SEQUENCE: 6
ggacggaaag accccgugg                                                       19

<210> SEQ ID NO 7
<211> LENGTH: 17
<212> TYPE: RNA
<213> ORGANISM: Artificial
<220> FEATURE:
<223> OTHER INFORMATION: Nucleid acid sequence activating TLR13
<220> FEATURE:
<221> NAME/KEY: misc_feature
<222> LOCATION: (6)..(6)
<223> OTHER INFORMATION: position of A methylated within total 23S rRNA

<400> SEQUENCE: 7
gacggaaaga ccccgug                                                         17

<210> SEQ ID NO 8
<211> LENGTH: 12
```

```
<212> TYPE: RNA
<213> ORGANISM: Artificial
<220> FEATURE:
<223> OTHER INFORMATION: Nucleid acid sequence activating TLR13
<220> FEATURE:
<221> NAME/KEY: misc_feature
<222> LOCATION: (6)..(6)
<223> OTHER INFORMATION: position of A methylated within total 23S rRNA

<400> SEQUENCE: 8
gacggaaaga cc                                                            12

<210> SEQ ID NO 9
<211> LENGTH: 19
<212> TYPE: RNA
<213> ORGANISM: Artificial
<220> FEATURE:
<223> OTHER INFORMATION: Nucleid acid sequence activating TLR13
<220> FEATURE:
<221> NAME/KEY: misc_feature
<222> LOCATION: (1)..(2)
<223> OTHER INFORMATION: mutated
<220> FEATURE:
<221> NAME/KEY: misc_feature
<222> LOCATION: (7)..(7)
<223> OTHER INFORMATION: position of A methylated within total 23S rRNA
<220> FEATURE:
<221> NAME/KEY: misc_feature
<222> LOCATION: (14)..(19)
<223> OTHER INFORMATION: mutated

<400> SEQUENCE: 9
aaacggaaag accaaaaaa                                                     19

<210> SEQ ID NO 10
<211> LENGTH: 19
<212> TYPE: RNA
<213> ORGANISM: Artificial
<220> FEATURE:
<223> OTHER INFORMATION: Nucleid acid sequence activating TLR13
<220> FEATURE:
<221> NAME/KEY: misc_feature
<222> LOCATION: (1)..(19)
<223> OTHER INFORMATION: Stabilized by thioate modification
<220> FEATURE:
<221> NAME/KEY: misc_feature
<222> LOCATION: (7)..(7)
<223> OTHER INFORMATION: position of A methylated within total 23S rRNA

<400> SEQUENCE: 10
ggacggaaag accccgugg                                                     19

<210> SEQ ID NO 11
<211> LENGTH: 48
<212> TYPE: RNA
<213> ORGANISM: Artificial
<220> FEATURE:
<223> OTHER INFORMATION: Nucleid acid sequence activating both TLR13 and
      TLR 17
<220> FEATURE:
<221> NAME/KEY: misc_feature
<222> LOCATION: (21)..(21)
<223> OTHER INFORMATION: position of A methylated within total 23S rRNA

<400> SEQUENCE: 11
gguuacccgc gacaggacgg aaagaccccg uggagcuuua cuguagcc                     48

<210> SEQ ID NO 12
<211> LENGTH: 33
<212> TYPE: RNA
<213> ORGANISM: Artificial
```

```
<220> FEATURE:
<223> OTHER INFORMATION: Nucleid acid sequence activating both TLR13 and
      TLR17
<220> FEATURE:
<221> NAME/KEY: misc_feature
<222> LOCATION: (6)..(6)
<223> OTHER INFORMATION: position of A methylated within total 23S rRNA

<400> SEQUENCE: 12
gacggaaaga ccccguggag cuuuacugua gcc                                  33

<210> SEQ ID NO 13
<211> LENGTH: 11
<212> TYPE: RNA
<213> ORGANISM: Artificial
<220> FEATURE:
<223> OTHER INFORMATION: TLR13 inhibiting nucleid acid
<220> FEATURE:
<221> NAME/KEY: misc_feature
<222> LOCATION: (7)..(9)
<223> OTHER INFORMATION: n =a, u, g or c

<400> SEQUENCE: 13
ugccuunnng g                                                          11

<210> SEQ ID NO 14
<211> LENGTH: 11
<212> TYPE: RNA
<213> ORGANISM: Artificial
<220> FEATURE:
<223> OTHER INFORMATION: TLR13 inhibiting nucleid acid

<400> SEQUENCE: 14
ugccuuucug g                                                          11

<210> SEQ ID NO 15
<211> LENGTH: 48
<212> TYPE: RNA
<213> ORGANISM: Artificial
<220> FEATURE:
<223> OTHER INFORMATION: TLR13 inhibiting nucleid acid
<220> FEATURE:
<221> NAME/KEY: misc_feature
<222> LOCATION: (1)..(48)
<223> OTHER INFORMATION: complementary strand
<220> FEATURE:
<221> NAME/KEY: misc_feature
<222> LOCATION: (21)..(21)
<223> OTHER INFORMATION: position of A methylated within total 23S rRNA

<400> SEQUENCE: 15 ccaugggcg cguguccugcc uuucuggggc accucgaaau gacaucgg                  48

<210> SEQ ID NO 16
<211> LENGTH: 12
<212> TYPE: RNA
<213> ORGANISM: Artificial
<220> FEATURE:
<223> OTHER INFORMATION: TLR13 activating sequence

<400> SEQUENCE: 16
gccggaaaga cc                                                         12

<210> SEQ ID NO 17
<211> LENGTH: 12
<212> TYPE: RNA
<213> ORGANISM: Artificial
<220> FEATURE:
<223> OTHER INFORMATION: TLR13 activating sequence
```

```
<400> SEQUENCE: 17
gacggaacga cc                                                              12

<210> SEQ ID NO 18
<211> LENGTH: 12
<212> TYPE: RNA
<213> ORGANISM: Artificial
<220> FEATURE:
<223> OTHER INFORMATION: TLR13 activating sequence

<400> SEQUENCE: 18
gacggaaaaa cc                                                              12

<210> SEQ ID NO 19
<211> LENGTH: 12
<212> TYPE: RNA
<213> ORGANISM: Artificial
<220> FEATURE:
<223> OTHER INFORMATION: TLR13 activating sequence

<400> SEQUENCE: 19
gacggaaagc cc                                                              12

<210> SEQ ID NO 20
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (6)..(6)
<223> OTHER INFORMATION: position of A methylated within total 23S rRNA
<220> FEATURE:
<221> NAME/KEY: misc_feature
<222> LOCATION: (7)..(7)
<223> OTHER INFORMATION: mutated

<400> SEQUENCE: 20
gacggacaga cc                                                              12

<210> SEQ ID NO 21
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (6)..(6)
<223> OTHER INFORMATION: mutated

<400> SEQUENCE: 21
gacgggaaga cc                                                              12

<210> SEQ ID NO 22
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (5)..(5)
<223> OTHER INFORMATION: mutated
```

```
<220> FEATURE:
<221> NAME/KEY: misc_feature
<222> LOCATION: (6)..(6)
<223> OTHER INFORMATION: position of A methylated within total 23S rRNA

<400> SEQUENCE: 22
gacgaaaaga cc                                                              12

<210> SEQ ID NO 23
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (1)..(1)
<223> OTHER INFORMATION: mutated
<220> FEATURE:
<221> NAME/KEY: misc_feature
<222> LOCATION: (3)..(4)
<223> OTHER INFORMATION: mutated
<220> FEATURE:
<221> NAME/KEY: misc_feature
<222> LOCATION: (6)..(6)
<223> OTHER INFORMATION: position of A methylated within total 23S rRNA

<400> SEQUENCE: 23
aaaagaaaga aa                                                              12

<210> SEQ ID NO 24
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (6)..(6)
<223> OTHER INFORMATION: position of A methylated within total 23S rRNA
<220> FEATURE:
<221> NAME/KEY: misc_feature
<222> LOCATION: (11)..(12)
<223> OTHER INFORMATION: mutated

<400> SEQUENCE: 24
gacggaaaga aa                                                              12

<210> SEQ ID NO 25
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (1)..(1)
<223> OTHER INFORMATION: mutated
<220> FEATURE:
<221> NAME/KEY: misc_feature
<222> LOCATION: (3)..(4)
<223> OTHER INFORMATION: mutated
<220> FEATURE:
<221> NAME/KEY: misc_feature
<222> LOCATION: (6)..(6)
<223> OTHER INFORMATION: position of A methylated within total 23S rRNA

<400> SEQUENCE: 25
aaaagaaaga cc                                                              12
```

<210> SEQ ID NO 26
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (6)..(6)
<223> OTHER INFORMATION: position of A methylated within total 23S rRNA
<220> FEATURE:
<221> NAME/KEY: misc_feature
<222> LOCATION: (12)..(12)
<223> OTHER INFORMATION: mutated

<400> SEQUENCE: 26
gacggaaaga ca                                                         12

<210> SEQ ID NO 27
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (1)..(1)
<223> OTHER INFORMATION: mutated
<220> FEATURE:
<221> NAME/KEY: misc_feature
<222> LOCATION: (3)..(3)
<223> OTHER INFORMATION: mutated
<220> FEATURE:
<221> NAME/KEY: misc_feature
<222> LOCATION: (6)..(6)
<223> OTHER INFORMATION: position of A methylated within total 23S rRNA

<400> SEQUENCE: 27
aaaggaaaga cc                                                         12

<210> SEQ ID NO 28
<211> LENGTH: 12
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (4)..(5)
<223> OTHER INFORMATION: mutated
<220> FEATURE:
<221> NAME/KEY: misc_feature
<222> LOCATION: (6)..(6)
<223> OTHER INFORMATION: position of A methylated within total 23S rRNA
<220> FEATURE:
<221> NAME/KEY: misc_feature
<222> LOCATION: (11)..(12)
<223> OTHER INFORMATION: mutated

<400> SEQUENCE: 28
gacccaaaga gg                                                         12

<210> SEQ ID NO 29
<211> LENGTH: 12
<212> TYPE: RNA
<213> ORGANISM: Artificial
<220> FEATURE:
<223> OTHER INFORMATION: S. aureus 23S rRNA mimicking and derived

```
                                    -continued
        oligoribonucleotides (ORNs)
<220> FEATURE:
<221> NAME/KEY: misc_feature
<222> LOCATION: (6)..(6)
<223> OTHER INFORMATION: methylated
<220> FEATURE:
<221> NAME/KEY: misc_feature
<222> LOCATION: (6)..(6)
<223> OTHER INFORMATION: position of A methylated within total 23S rRNA

<400> SEQUENCE: 29
gacggaaaga cc                                                             12

<210> SEQ ID NO 30
<211> LENGTH: 12
<212> TYPE: RNA
<213> ORGANISM: Artificial
<220> FEATURE:
<223> OTHER INFORMATION: S. aureus 23S rRNA mimicking and derived
        oligoribonucleotides (ORNs)
<220> FEATURE:
<221> NAME/KEY: misc_feature
<222> LOCATION: (6)..(6)
<223> OTHER INFORMATION: position of A methylated within total 23S rRNA
<220> FEATURE:
<221> NAME/KEY: misc_feature
<222> LOCATION: (6)..(7)
<223> OTHER INFORMATION: methylated

<400> SEQUENCE: 30
gacggaaaga cc                                                             12

<210> SEQ ID NO 31
<211> LENGTH: 20
<212> TYPE: RNA
<213> ORGANISM: Artificial
<220> FEATURE:
<223> OTHER INFORMATION: S. aureus 23S rRNA mimicking and derived
        oligoribonucleotides (ORNs)
<220> FEATURE:
<221> NAME/KEY: misc_feature
<222> LOCATION: (8)..(8)
<223> OTHER INFORMATION: position of A methylated within total 23S rRNA

<400> SEQUENCE: 31
ccgacacagg uagucaagau                                                     20

<210> SEQ ID NO 32
<211> LENGTH: 15
<212> TYPE: RNA
<213> ORGANISM: Artificial
<220> FEATURE:
<223> OTHER INFORMATION: S. aureus 23S rRNA mimicking and derived
        oligoribonucleotides (ORNs)
<220> FEATURE:
<221> NAME/KEY: misc_feature
<222> LOCATION: (9)..(9)
<223> OTHER INFORMATION: position of A methylated within total 23S rRNA
<220> FEATURE:
<221> NAME/KEY: misc_feature
<222> LOCATION: (10)..(10)
<223> OTHER INFORMATION: n =pseudouridine

<400> SEQUENCE: 32
gcaccucgan gucgc                                                          15

<210> SEQ ID NO 33
<211> LENGTH: 12
<212> TYPE: RNA
<213> ORGANISM: Artificial
<220> FEATURE:
```

```
<223> OTHER INFORMATION: S. aureus 23S rRNA mimicking and derived
      oligoribonucleotides (ORNs)
<220> FEATURE:
<221> NAME/KEY: misc_feature
<222> LOCATION: (6)..(6)
<223> OTHER INFORMATION: position of A methylated within total 23S rRNA
<220> FEATURE:
<221> NAME/KEY: misc_feature
<222> LOCATION: (7)..(7)
<223> OTHER INFORMATION: methylated

<400> SEQUENCE: 33
gacggaaaga cc                                                          12

<210> SEQ ID NO 34
<211> LENGTH: 10
<212> TYPE: RNA
<213> ORGANISM: Artificial
<220> FEATURE:
<223> OTHER INFORMATION: S. aureus 23S rRNA mimicking and derived
      oligoribonucleotides (ORNs)
<220> FEATURE:
<221> NAME/KEY: misc_feature
<222> LOCATION: (3)..(3)
<223> OTHER INFORMATION: position of A methylated within total 23S rRNA
<220> FEATURE:
<221> NAME/KEY: misc_feature
<222> LOCATION: (10)..(10)
<223> OTHER INFORMATION: n is a, c, g, or u

<400> SEQUENCE: 34 ggaaagaccn                                                             10

<210> SEQ ID NO 35
<211> LENGTH: 11
<212> TYPE: RNA
<213> ORGANISM: Artificial
<220> FEATURE:
<223> OTHER INFORMATION: truncated version of SED ID NO: 8

<400> SEQUENCE: 35
acggaaagac c                                                           11
```